(12) United States Patent
Xu

(10) Patent No.: US 11,396,515 B2
(45) Date of Patent: Jul. 26, 2022

(54) PYRAN FUSED RING COMPOUND, PREPARATION METHOD THEREFOR AND USE THEREOF

(71) Applicant: BEIJING TIENYI LUFU PHARMATECH CO. LTD., Beijing (CN)

(72) Inventor: Weiping Xu, Beijing (CN)

(73) Assignee: BEIJING TIENYI LUFU PHARMATECH CO. LTD., Beijing (CN)

(*) Notice: Subject to any disclaimer, the term of this patent is extended or adjusted under 35 U.S.C. 154(b) by 194 days.

(21) Appl. No.: 16/616,340

(22) PCT Filed: Mar. 1, 2019

(86) PCT No.: PCT/CN2019/076757
§ 371 (c)(1),
(2) Date: Mar. 12, 2020

(87) PCT Pub. No.: WO2019/166019
PCT Pub. Date: Sep. 6, 2019

(65) Prior Publication Data
US 2022/0048921 A1 Feb. 17, 2022

(30) Foreign Application Priority Data

Mar. 2, 2018 (CN) .......................... 201810176172.2

(51) Int. Cl.
*C07D 493/04* (2006.01)
*C07D 309/10* (2006.01)

(52) U.S. Cl.
CPC .......... *C07D 493/04* (2013.01); *C07D 309/10* (2013.01)

(58) Field of Classification Search
CPC .......................... C07D 493/04; C07D 309/10
USPC ........................................................ 549/396
See application file for complete search history.

(56) References Cited

U.S. PATENT DOCUMENTS 7,982,060 B2 * 7/2011 Austad .................... A61P 35/02
549/472

FOREIGN PATENT DOCUMENTS

| CN | 1993342 A | 7/2007 |
|---|---|---|
| WO | 2017168309 A1 | 10/2017 |
| WO | 2018006031 A1 | 1/2018 |

* cited by examiner

*Primary Examiner* — Deepak R Rao
(74) *Attorney, Agent, or Firm* — Novick, Kim & Lee, PLLC; Allen Xue

(57) ABSTRACT

The present invention relates to pyran-fused ring compounds, preparation methods thereof and use thereof, especially to pyran-fused ring compounds usable for preparing Halichondrin, Eribulin, or analogues thereof, preparation methods thereof and use thereof. Use of any of the compounds of formula (I) to (XIII) of the present invention in preparation of Halichondrin B, Eribulin, analogues thereof or C1-C13 moieties thereof. Provided in the present invention are intermediates usable for preparing Halichondrin B, Eribulin, or analogues thereof, especially the key product of C1-C13 moieties, preparation methods thereof and use thereof. The starting material for the synthesis pathway of the present invention is inexpensive and readily available with sustainable source and reliable quality. Since the structural characteristics of the reactants of theirself are made full use in choosing the method of constructing the chiral centers, the efficiency in the synthesis is considerably increased, the difficulty in and the risk on quality control of the product are reduced; and using a highly toxic and expensive high-valent osmium catalyst is avoided, which have the cost and environmental friendliness significantly improved.

11 Claims, No Drawings

PYRAN FUSED RING COMPOUND, PREPARATION METHOD THEREFOR AND USE THEREOF

TECHNICAL FIELD

The present invention relates to pyran-fused ring compound, preparation methods thereof and use thereof, especially to pyran-fused ring compounds usable for preparing Halichondrin, Eribulin, or analogues thereof, preparation methods thereof and use thereof, and the present invention belongs to the field of organic synthesis.

BACKGROUND ART

The pyran-fused ring compounds, especially natural products having complicated structures tend to have extensive biologic activities or pharmacological activities. For example, Halichondrin B (Halichondrin B, hereinafter referred to as HB) is a natural product with a complicated structure which is found in the sponge and has a potent anti-tumor effect and broad prospect in pharmaceutics, while Eribulin (Eribulin, hereinafter referred to as EB) is an analogue with a simplified structure of HB which has been used clinically for treatment of advanced breast cancer and liposarcoma.

Neither HB nor EB can be obtained from the natural source and they are available only through artificial synthesis. Since the two compounds have similar structures, especially for the C1-C29 moieties having identical structure, an appropriate intermediate can be used in the synthesis of such compounds. For example, an intermediate shown below in the formula (1) can be used to constitute the C1-C13 moieties of Eribulin.

Halichondrin B

Eribulin mesylate

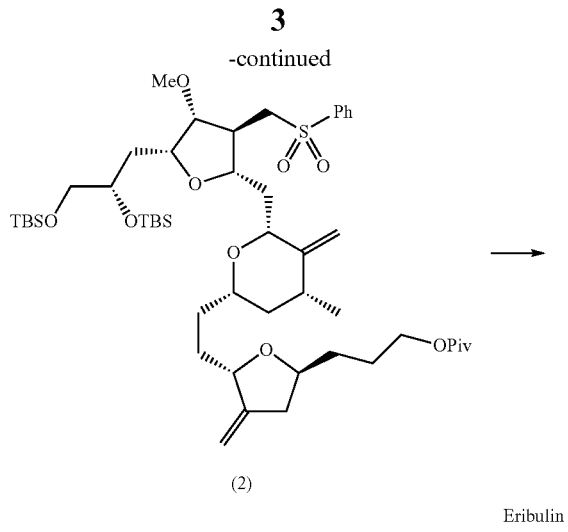

The known methods for synthesizing compound (1) in the state of the art include the following two ones:

Method 1: L-gulono-γ-lactone or D-mannono-γ-lactone is used as the starting material and subjected to appropriate hydroxyl protection before being reduced to a hemiacetal (3); the resulting hemiacetal is subjected to the Wittig reaction to effect carbon-chain elongation, resulting in an enolic methyl ether (4); a C7-hydroxyl (5) is introduced by an OsO4-catalyzed dihydroxylation reaction and then acylated; the acylated product (6) is reacted with 3-trimethylsilyl-4-pentenate to introduce the C1-C5 moieties, and the resulting product is subsequently subjected to double bond shift and intra-molecular Michael addition under a basic condition; the resulting addition product is subjected to selective deprotection of C11-C12 dihydroxyl and oxidative cleavage to generate the aldehyde (9); the aldehyde (9) is reacted with 2-trimethylsilylvinyliodide, and then subjected to the steps such as iodination, hydroxyl protection, etc. to synthesize the compound (11), that is, the above-mentioned compound (1) in which the hydroxyl is protected by t-butyl dimethylsilyl (TBS).

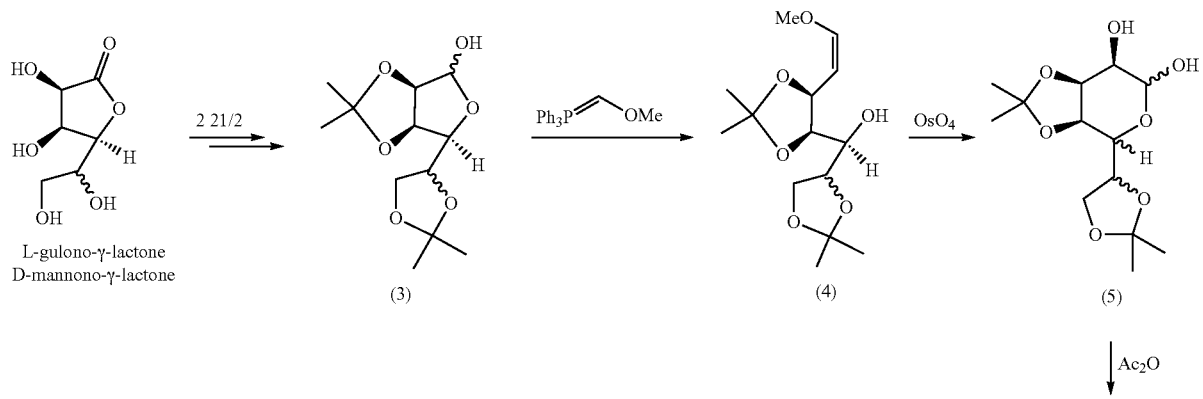

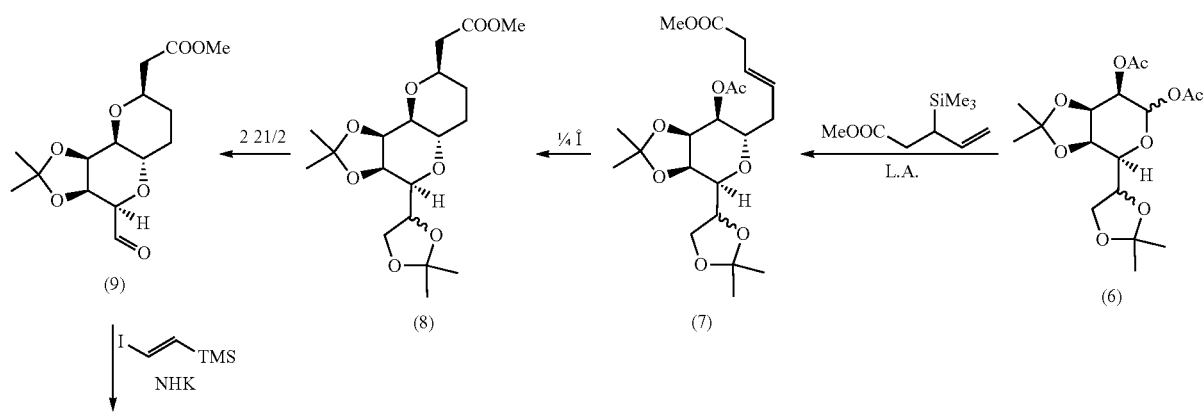

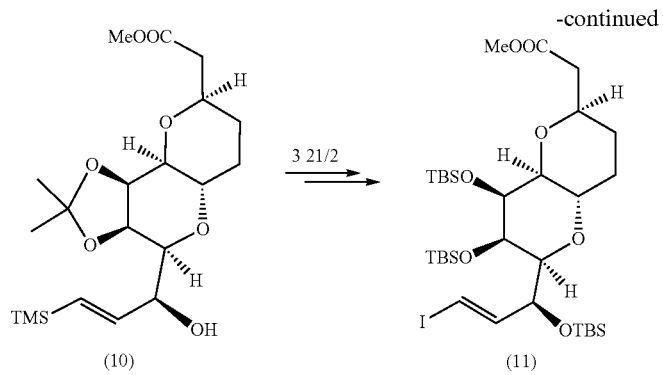

Method 2: The furanylalcoholderivative (13) is used as the starting material and subjected to the reactions such as oxidization to the pyran (14), olefin cross-metathes is to introduce the C1 ester group (15) and intra-molecular Oxa-Michael addition, etc., to synthesize the bicyclic intermediate (16); the compound (16) is oxidized to a lactone (17), subsequently subjected to the OsO$_4$-catalyzed dihydroxylation reaction in order to introduce C8, C9 dihydroxyl to obtain intermediate (18), then subjected to action of the Tebbe reagent and boron hydrogenation-oxidation in order to introduce C11, and finally oxidized with Dess-Martin in order to synthesize the aldehyde (19); synthesis of the compound (1) is then completed using the above-mentioned conversion methods for the compounds (9) to (11).

In addition, it has been also reported recently that D-Glucuronolactone is used as the starting material and converted to the compound (20) through several reaction steps and then converted to a compound (21) bearing furan moiety through multiple reaction steps; C7, C8 dihydroxyl is introduced to the compound (21) to obtain a compound (22) under the Sharpless dihydroxylation condition, and finally a compound (25) is synthesized through two key intermediates, the compound (23) and the compound (24). The compound (25) has the C1-C14 structural characteristic of the HB or EB and can be used to prepare the compound of interest.

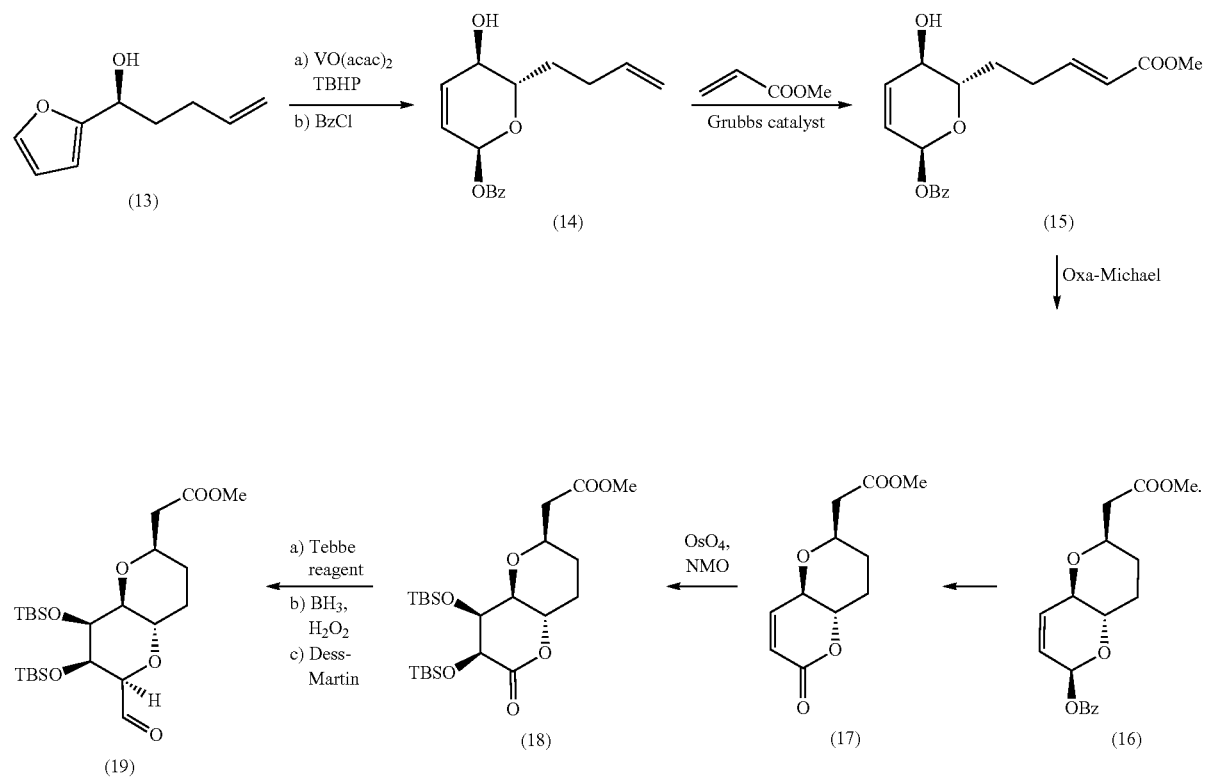

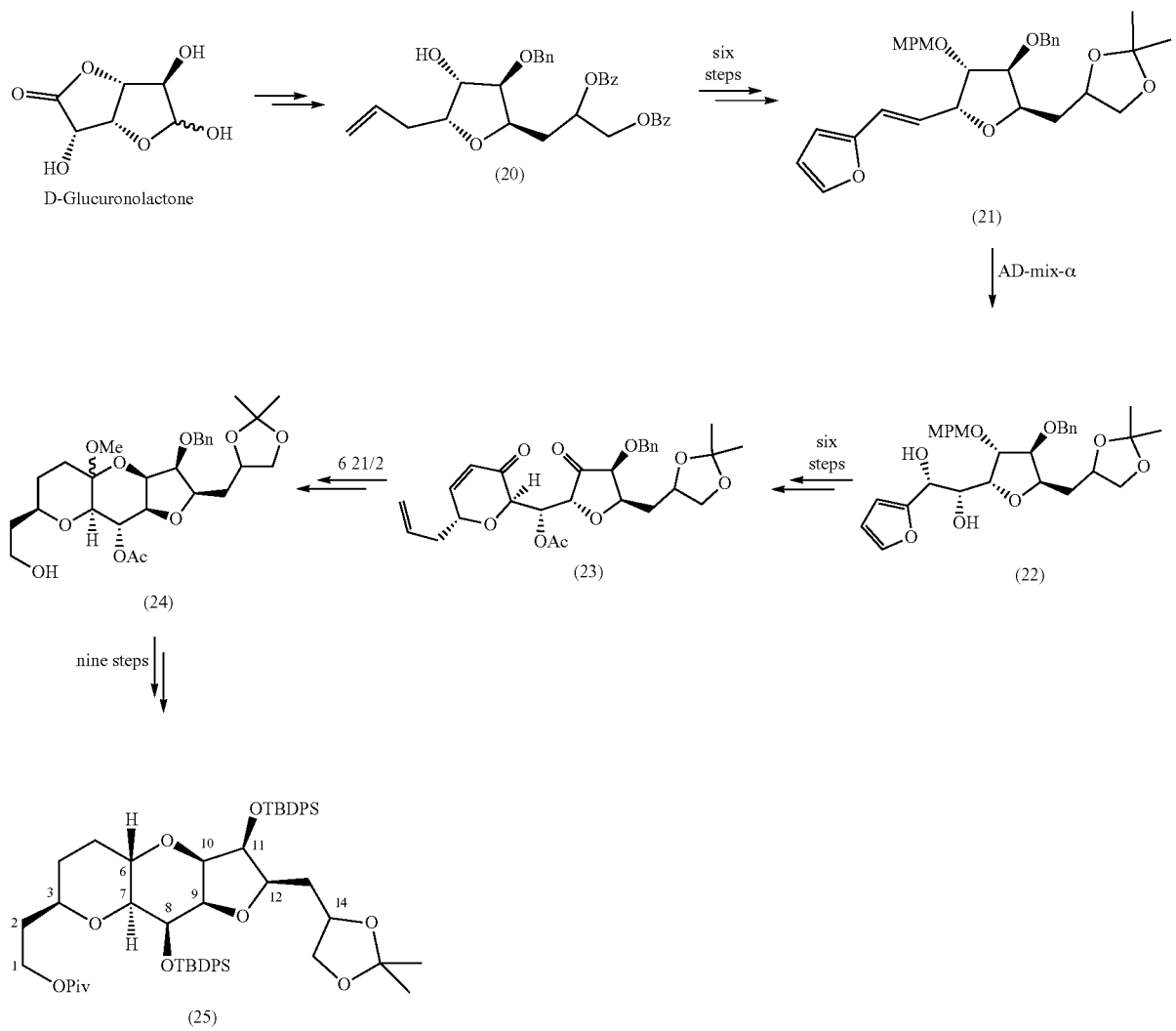

Nonetheless, the start-of-art methods have various shortcomings. For example, the synthesis pathway is too lengthy, the optical purity of the starting material is difficult to control, and all of the methods are involved in using highly toxic and expensive high-valent osmium catalysts, which are disadvantageous to cost control and labor protection. Moreover, some reactions used in the aforesaid synthesis also have the disadvantage of poor stereoselectivity, which are disadvantageous to guaranteeing purity of the product. Thus, there is a great need in the preparation methods and the intermediates which can improve the synthesis efficiency, selectivity or are environmentally friendly, in order to improve the synthesis procedure of the above-mentioned pyran-fused ring compounds.

SUMMARY OF THE INVENTION

In order to solve the above-mentioned problems, the present invention provides a compound of following formula (V):

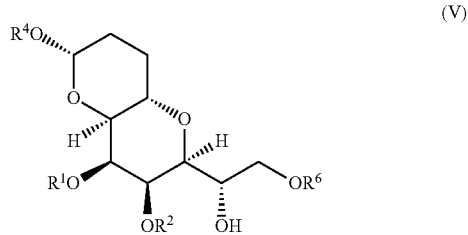

wherein $R^4$, $R^6$ are the same or different and selected independently of one another from the group consisting of hydroxyl protecting groups;

$R^1$, $R^2$ are the same or different and selected independently of one another from the group consisting of H or $—B(OR^7)_2$;

$R^7$ is selected from the group consisting of an alkyl unsubstituted or optionally substituted with one or more of $R^a$, or the two adjacent $R^7$ groups bind to each other to form an alkylidene unsubstituted or optionally substituted with one or more of $R^a$, two ends of said alkylidene each binding to an O atom via a chemical bond, therefor resulting in formation of a ring with the B atom;

each of the $R^a$ is the same or different and selected independently of one another from the group consisting of —F, —Cl, —Br, —I, =O, alkyl, cycloalkyl, heterocycyl, aryl, heteroaryl, alkoxy, alkenyloxy, cycloalkoxy, heterocyclyloxy, aryloxy, heteroaryloxy, cycloalkylalkyl, heterocyclylalkyl, arylalkyl, or heteroarylalkyl.

According to the present invention, $R^4$ may be selected from e.g. alkyl; $R^6$ may be selected from e.g. silanyl, benzyl, substituted benzyl and acyl, preferably benzyl, p-methoxybenzyl (PMB) or pivaloyl.

According to embodiments of the present invention, the two adjacent $R^7$ groups bind to each other to form an alkylidene unsubstituted or optionally substituted with one or more of $R^a$, two ends of said alkylidene each binding to an O atom via a chemical bond, therefore resulting in the formation of a 5-8 membered ring with the B atom. As an example, the two adjacent $R^7$ groups bind to each other to

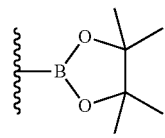 [SMILES: *B1OC(C)(C)C(C)(C)O1]

form —C(CH$_3$)$_2$—C(CH$_3$)$_2$—, thereby binding to an O atom via a chemical bond, to form together with the B atom.

The present invention further provides a compound of following formula (IV):

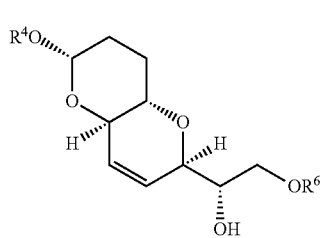

wherein $R^4$, $R^6$ are defined as described above.

Preferably, the compound of formula (IV) has structure of following formulas 33, 33B; and the compound of formula (V) has structure of following formulas 38, 38B:

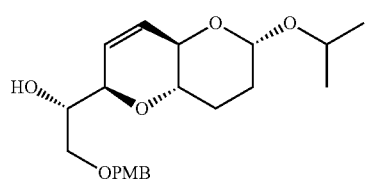

33

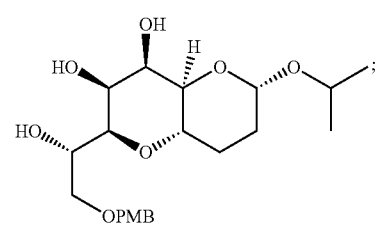

38

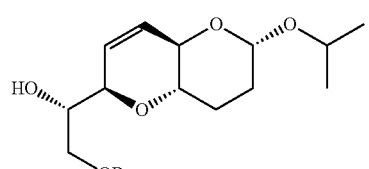

33B

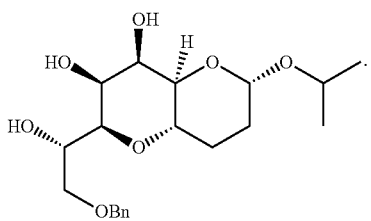

38B

The present invention further provides a method of preparing the compound of formula (V), comprising the step of reacting the compound of formula (IV) in the presence of an alkali, then oxidizing the resulting intermediate in the presence of an oxidizing agent to obtain the compound of formula (V).

According to the present invention, the alkali may be selected from an organic base, an inorganic base or the mixtures thereof, e.g. one or more of potassium carbonate, sodium carbonate, potassium hydrogen carbonate, sodium bicarbonate, cesium carbonate, sodium hydroxide, potassium hydroxide, sodium acetate, triethyl amine, pyridine, piperidine.

According to embodiments of the present invention, the method of preparing the compound of formula (V) comprises: reacting the compound of formula (IV) with B$_2$(OR$^7$)$_4$ in the presence of the alkali, to obtain the intermediate of formula (IV-1) which is oxidized subsequently in the presence of the oxidizing agent to remove the group —B(OR$^7$)$_2$ to obtain the compound of formula (V):

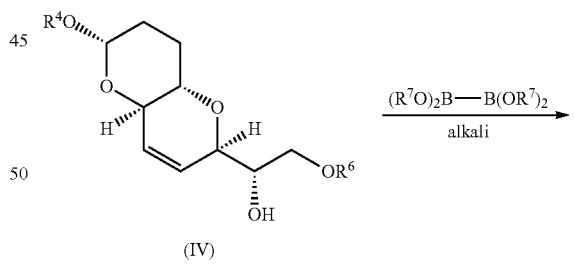

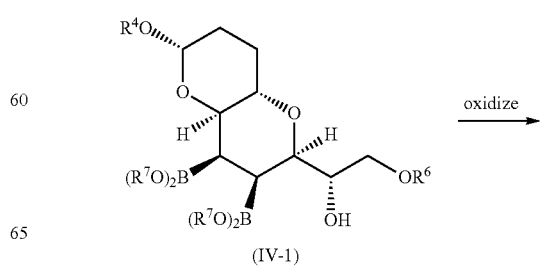

-continued

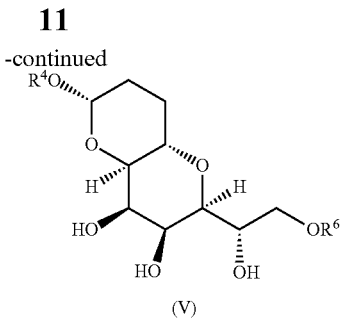

(V)

wherein R⁷ is defined as described above.

Preferably, in the reaction for converting compound (IV) to the compound (IV-1):

said $B_2(OR^7)_4$ is $(R^7O)_2B-B(OR^7)_2$, preferably bis(pinacol) diborate ($B_2(pin)_2$); and said alkali may be cesium carbonate.

Preferably, the molar ratio of the $B_2(OR^7)_4$: the alkali: the compound of formula (IV) may be 2-6:0.3-2:1, preferably 4:1:1;

the reaction may be performed in a solvent such as methanol, tetrahydrofurane or a mixed solvent thereof; preferably, the ratio of methanol to tetrahydrofurane (the volume ratio) in the mixed solvent may be about 1:1 to about 1:5, preferably about 1:3;

the ratio of the total volume of the solvent to the compound of formula (IV) (mL:g) may be (5-10): 1, such as (7-8): 1;

The reaction can be performed at 60-80° C., e.g. a reflux temperature.

Preferably, in the reaction for converting compound (IV-1) to the compound (V):

the oxidizing agent may be a peroxide, such as sodium peroxoborate or a hydrate thereof (sodium peroxoborate tetra-hydrate). The molar ratio of the oxidizing agent to the compound of formula (N) may be 2-10:1, preferably 4-8:1, such as 7-8:1;

Preferably, after the reaction of preparing the compound (IV-1) is completed, the solvent is evaporated off, the mixed solvent of tetrahydrofuran and water is added to dissolve the residue, the oxidizing agent is added batch wise under cooling with ice-water bath, and the reaction is raised to room temperature to proceed, filtered after completion of the reaction, extracted with an organic solvent, such as dichloromethane, concentrated, and separated to obtain the compound (V);

Preferably, in the mixed solvent of tetrahydrofurane and water, the volume ratio of tetrahydrofurane to water may be (1-2): 1, such as (1.3-1.5): 1; and the ratio of the total volume of the mixed solvent to the compound of formula (IV) (mL:g) may be (20-50):1, such as (25-35): 1.

According to the present invention, the compound of formula (N) may be prepared by one of the methods below:

1) a diene compound (III) is subjected to an epoxidation reaction to generate a compound (III-1) selectively epoxidized at the positions C8, C9; then the compound (III-1) is subjected to hydroxyl protection to generate a compound (III-2); the protecting group R⁵ in the compound (III-2) is removed under an appropriate condition to generate a secondary alcohol compound (III-3); the compound (III-3) undergoes an intra-molecular $S_N2$ reaction under the action of an alkali, yielding the compound (IV):

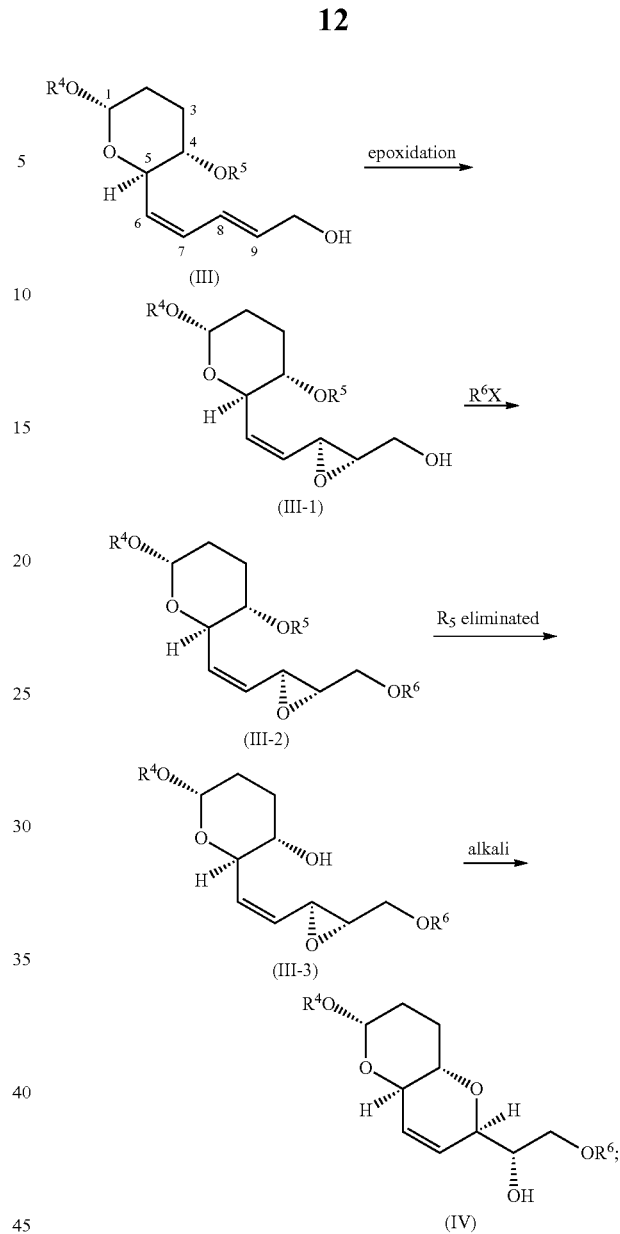

or 2) the compound (III) is subjected to the removal of R⁵, resulting in a triol compound (III-4); then the compound (III-4) is epoxidized selectively at the positions C8, C9, resulting in an epoxy compound (III-5), and a bicyclic glycol compound (III-6) is subsequently produced; then the compound (III-6) is reacted with a hydroxyl-protecting agent, yielding the compound (IV):

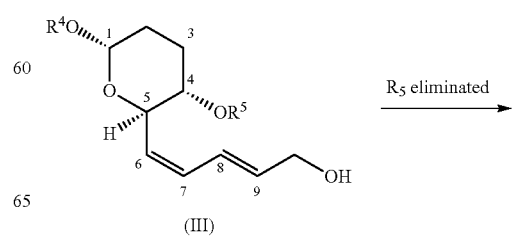

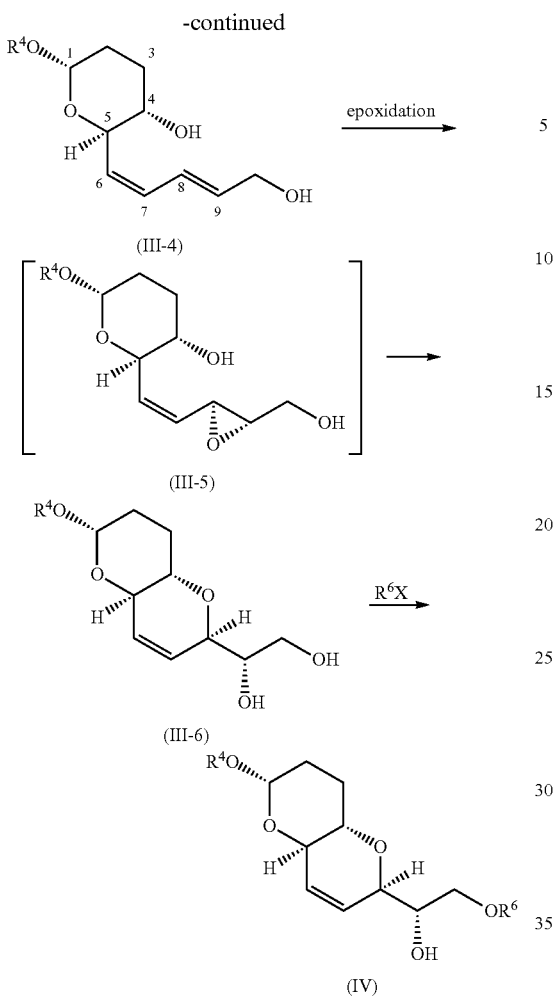

wherein $R^4$, $R^6$ are defined as described above;
$R^5$ is selected from hydroxyl protecting groups.

Preferably, in Method 1):

the compound (III-1) is reacted with a hydroxyl-protecting agent $R^6X$ (e.g., p-methoxybenzyl bromide) in the presence of an alkali such as NaH, resulting in the compound (III-2); wherein the molar ratio of the alkali or the hydroxyl-protecting agent to the compound (III-1) may be (1.0-1.5): 1, e.g. (1.04-1.08):1; The reaction can be performed at a temperature of 0 to −10° C. (e.g. to −5° C.) in a solvent, such as tetrahydrofuran;

The compound (III-2) is reacted in the presence of tetrabutylammonium fluoride in a solvent, such as tetrahydrofuran, resulting in the compound (III-3);

The compound (III-3) undergoes an intra-molecular $S_N2$ reaction with the action of an alkali, resulting in the compound (IV), wherein the alkali may be selected from an organic base or inorganic base, e.g. potassium tert-butylate;

Preferably, in Method 2), the compound (III) is reacted in the presence of tetrabutylammonium fluoride in a solvent, such as tetrahydrofuran, resulting in the compound (III-4).

According to embodiments of the present invention, selectively epoxidation at the positions C8, C9, namely, conversion from the compound (III) to the compound (III-1) or from the compound (III-4) to the compound (III-5), may be achieved by oxidation in the presence of an oxidizing agent selected from the following: peroxy acid, Lewis acid-catalyzed peroxy alcohol (e.g., peroxy tert-butanol, cumene hydroperoxide CHP). Preferably, said oxidation is the one catalyzed with a Lewis acid. As an example, said oxidation is performed in the presence of VO(acac)$_2$/t-BuOOH and/or Ti(O-iPr)$_4$/(+)-DET/CHP.

Preferably, the epoxy compound (III-5) undergoes the intra-molecular $S_N2$ reaction spontaneously in the reaction system for compound (III-4) epoxidation, resulting in the compound (III-6);

As an example, the reaction system for compound (III-4) epoxidation comprises a reaction in the presence of L-(+)-diethyl tartarate, tetraisopropoxy titanium and cumene hydroperoxide (Ti(O-iPr)$_4$/(+)-DET/CHP) in a solvent such as dichloromethane, wherein the molar ratio of L-(+)-diethyl tartarate:tetraisopropoxy titanium:cumene hydroperoxide: the epoxy compound (III-5) may be (1.2-1.8):(1.0-1.4):(3.8-4.2): 1, e.g. about 1.2:1.0:3.3:0.8. The reaction temperature may be below 0° C., preferably below −15° C., such as −25° C. to −40° C. Preferably, after completion, the reaction is quenched with tributyl phosphine and then an aqueous solution of L(+)-tartaric acid is added, followed by separation, resulting the compound (III-6).

Preferably, the compound (III-6) is reacted with the hydroxyl-protecting agent $R^6X$ in the presence of an alkali such as NaH, yielding the compound (IV), wherein the molar ratio of the alkali or the hydroxyl-protecting agent to the compound (III-6) may be (1.0-1.5): 1, e.g. (1.04-1.08):1; The reaction can be performed at a temperature of 0 to −10° C. (e.g. to −5° C.) in a solvent, such as tetrahydrofuran.

The present invention further provides the compound of formula (III) and a preparation method thereof, wherein the preparation method comprises reacting the compound of formula (II) with a phosphorus ylide:

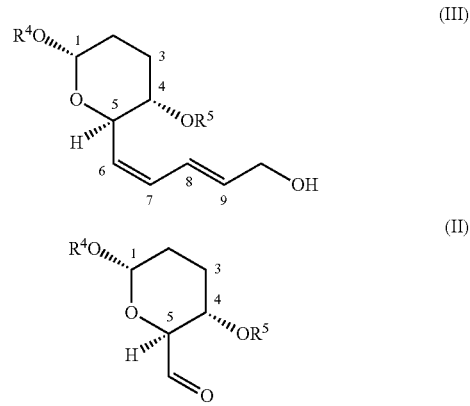

wherein $R^4$ is defined as described above;
$R^5$ is selected from hydroxyl protecting groups.

According to the present invention, in the compound of formula (II) or (III), the configuration of C1 may be R or S, or a mixture thereof; and the absolute configuration for C4 and C5 is S and R, respectively.

According to the present invention, the compound of formula (II) may be reacted with

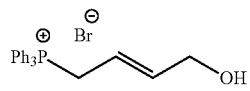

in the presence of an alkali to prepare the compound of formula (III). Preferably, the alkali may be selected from one of potassium tert-butylate, butyl lithium and phenyl lithium or a mixture of the aforesaid.

Optionally, the compound of formula (II) can be obtained by reacting the compound of formula (I) under an oxidizing condition:

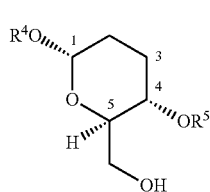
(I)

wherein $R^4$, $R^5$ are independently defined as described above.

As an example, the oxidizing condition may be selected from a reagent or system known in the art which enables oxidation of a primary alcohol to an aldehyde, e.g. DMP (Dess-Martin Periodinane, namely 1,1,1-tri(acetoxy)-1,1-dihydro-1,2-benziodoxol-3(1H)-one), a DMS 0-based oxidation system (e.g., a DMSO/organic base system, in which the organic base is selected from e.g. triethyl amine, N,N-diisopropylethyl amine, sulphur trioxide-pyridine complex ($SO_3$ py), e.g., Swern oxidation system), a Jones reagent (namely, the system of chromium trioxide, sulphuric acid and water), DCC (dicyclohexylcarbodiimide), PCC (pyridinium chlorochromate).

According to embodiments of the present invention, the compound of formula (I) may be prepared by one or more steps starting with the known compounds of I-01 to 1-05 as the starting material:

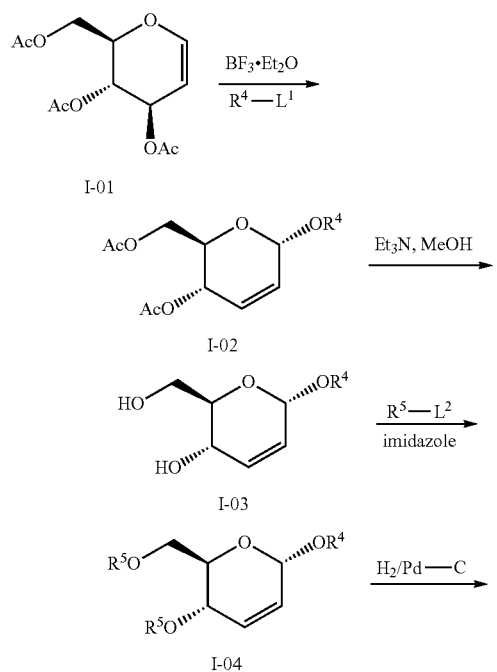

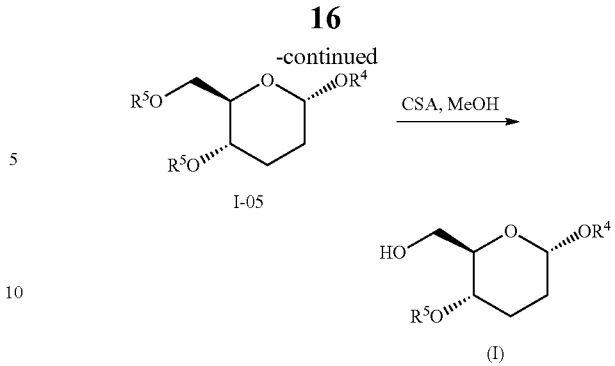

wherein $R^4$, $R^5$ are defined as described above;
$L^1$, $L^2$ are the leaving group, such as halogen (e.g., Cl, Br or I) or OH.

The present invention further provides the compound of formula (VI) and a preparation method thereof, wherein the preparation method comprises reacting the compound of formula (V-1) with a hydroxyl-protecting agent, resulting in the compound of formula (VI):

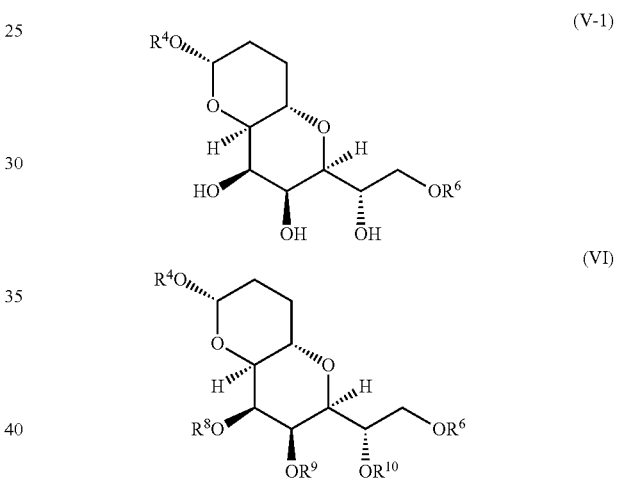

wherein $R^4$, $R^6$ are defined as described above;
wherein $R^8$, $R^9$, $R^{10}$ are the same or different and selected independently of one another from the group consisting of hydroxyl protecting groups, e.g. a hydroxyl protecting group comprising less than 6 carbon atoms, such as, an acyl comprising 6, 5, 4, 3, 2 or 1 carbon atom, e.g., formyl, acetyl, or propionyl.

According to the present invention, the hydroxyl-protecting agent may be selected from compounds known in the art, which comprises a hydroxyl protecting functional group and a leaving group optionally present. As an example, the hydroxyl-protecting agent may be a compound which provides a hydroxyl group with acyl group, ester group, carbonate group, carbamate group, sulfonate group or ether group, e.g. acid anhydride (e.g., acetic anhydride), acyl halogenide (e.g., acetyl chloride), silane compounds such as TMSCl, TMSOTf, TESCl, TESOTf, TBDPSCl, TIPSCl, trimethylsilyl imidazole; alkyl etherification reagents such as MeI, $(MeO)_2SO_2$, MeOTf; benzyl etherification reagents such as $PhCH_2Br$, $PhCH_2Cl$, BnBr; TrCl, allyl halogenides and so forth.

Preferably, the compound of formula (V-1) is reacted with the hydroxyl-protecting agent in the presence of an alkali, resulting in the compound of formula (VI).

According to the present invention, the reaction of the compound of formula (V-1) with the hydroxyl-protecting agent may be performed concomitantly, to protect three hydroxyl groups all at once, or step by step, to protect three hydroxyl groups separately. As an example, the compound (V-1) is reacted with acetic anhydride in the presence of an alkali, resulting in the compound of formula (VI). Preferably, the above reaction is preferably performed in the presence of a catalyst, such as DMAP.

The present invention further provides a compound of following formula (VII):

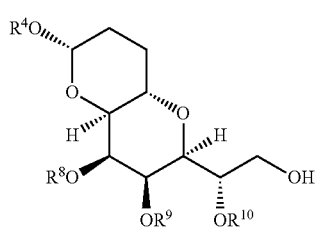

(VII)

wherein $R^4$, $R^8$, $R^9$, $R^{10}$ are independently defined as described above.

The present invention further provides a method of preparing the compound of formula (VII), wherein the method comprises reacting the compound of formula (VI) under a condition for removing the $R^6$ group, to obtain the compound of formula (VII).

As an example, the condition for removing the $R^6$ group may be a reaction performed in the presence of DDQ (2,3-dichloro-5,6-dicyano-para-benzoquinone). The reaction may be performed in a mixed solvent of dichloromethane and water. In mixed solvent, the volume ratio of dichloromethane to water may be an (5-50):1, e.g., (8-15):1, such as 10:1. Preferably, the reaction is performed at a temperature ranging from ice water bath to room temperature.

The present invention further provides a compound of following formula (VIII):

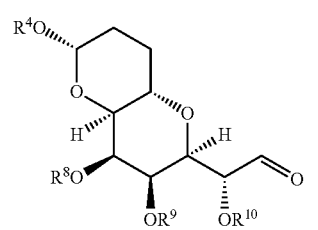

(VIII)

wherein $R^4$, $R^8$, $R^9$, $R^{10}$ are independently defined as described above.

The present invention further provides a method of preparing the compound of formula (VIII), wherein the method comprises reacting the compound of formula (VII) in the presence of an oxidizing agent.

According to embodiments of the present invention, the oxidizing agent may be selected from a reagent or system known in the art which enables oxidation of a primary alcohol to an aldehyde, e.g. DMP (Dess-Martin Periodinane, namely 1,1,1-tri(acetoxy)-1,1-dihydro-1,2-benziodoxol-3 (1H)-one), a DMSO-based oxidation system (e.g., a DMSO/ organic base system, in which the organic base is selected from e.g. triethyl amine, N,N-diisopropylethyl amine, sulphur trioxide-pyridine complex ($SO_3$.py), e.g., Swern oxidation system), a Jones reagent (namely, the system of chromium trioxide, sulphuric acid and water), DCC (dicyclohexylcarbodiimide), PCC (pyridinium chlorochromate).

Preferably, said reaction is performed in the presence of DMSO, oxalyl chloride and triethyl amine, in which the molar ratio of DMSO, oxalyl chloride, triethyl amine and the compound (VII) may be (1-3):(1-2):(3-8): 1, e.g., 2:1.5:5:1;

Preferably, the reaction is performed at a temperature of lower than 0° C., e, g. lower than −10° C., such as, lower than −25° C., e. g. lower than −70° C. The solvent for the reaction may be haloalkane, such as dichloromethane.

Preferably, the reaction is performed by dropping the solution of the compound (VII) in said solvent into the oxidation system.

Preferably, after completion of the reaction, the reaction is quenched with saturated $NaHCO_3$ solution, the aqueous phase is extracted with haloalkane, such as dichloromethane, the organic phase is concentrated before being used directly for preparing other compounds.

The present invention further provides a compound of following formula (IX):

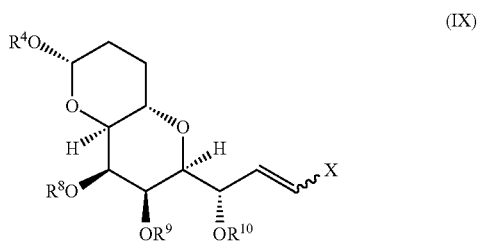

(IX)

wherein $R^4$, $R^8$, $R^9$, $R^{10}$ are independently defined as described above and X is selected from Cl, Br, I or $R^{11}S(O)_2$—;

$R^{11}$ is selected from the group consisting of alkyl, cycloalkyl, heterocyclyl, aryl, or heteroaryl unsubstituted or optionally substituted with one or more $R^a$. For example, $R^{11}S(O)_2$— may be benzenesulfonyloxy, p-tosyloxy, methylsulfonyloxy or triflouromethylsulfonyloxy.

Preferably, in the compound of formula (IX), the configuration of the double bond attached to X may be Z, E or a mixture thereof, preferably E.

As an example, the compound of formula (VIII) has a structure of following formulas 41, 49; and the compound of formula (IX) has a structure of following formulas 42, 11:

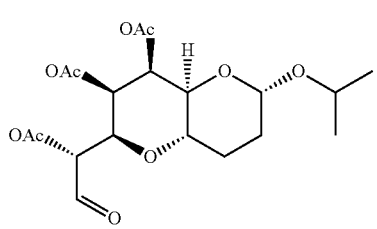

41

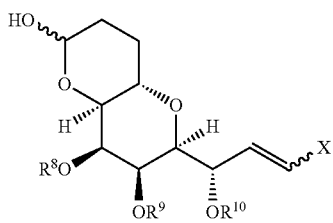

wherein $R^8$, $R^9$, $R^{10}$, X are independently defined as described above.

Preferably, the tautomeric isomers comprise, but are not limited to the tautomeric isomers having hemiacetal structure of the compound of formula (X), e.g., the following tautomeric isomers:

42

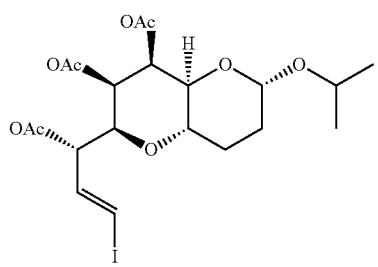

49

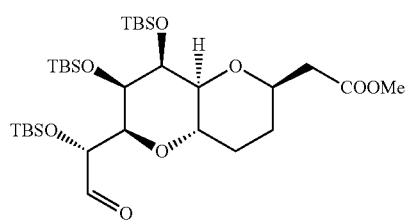

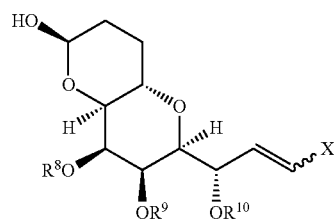

11

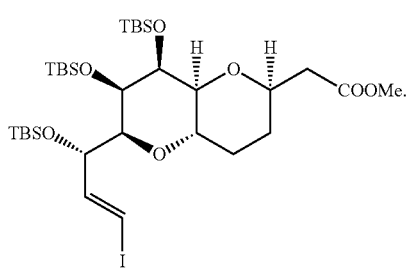

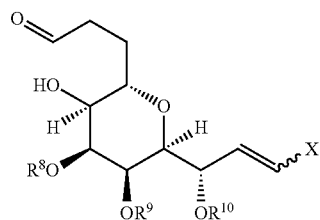

The present invention further provides a method of preparing the compound of formula (IX), wherein the method comprises reacting the compound of formula (VIII) with $CHX_3$ in the presence of chromium halide, wherein X is defined as described above; preferably, chromic halide may be $CrCl_2$; and $CHX_3$ may be CHIS.

According to embodiments of the present invention, the molar ratio of chromous halide to the compound of formula (VIII) may be (3-8):1, preferably 5:1; and the molar ratio of $CHX_3$ to the compound of formula (VIII) may be (1-3):1, preferably 2:1.

As an example, the reaction can be performed in a mixed solvent of tetrahydrofuran and dioxane. Preferably, the reaction is performed by dropping the solution of the compound (VIII) and $CHX_3$ in dioxane solution into the suspension of chromous halide in the mixed solvent of tetrahydrofuran and dioxane.

Preferably, the ratio of tetrahydrofuran to dioxane in the mixed solvent may be in a rang of from 1:5 to 5:1, preferably from 1:3 to 3:1.

The present invention further provides the compound of formula (X) and a preparation method thereof, wherein the preparation method comprises reacting the compound of formula (IX) under a condition for removing the $R^4$ group, yielding the compound of formula (X) and/or tautomeric isomers thereof:

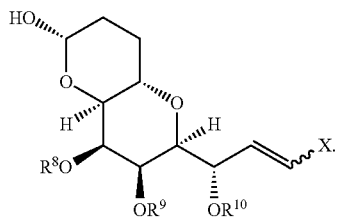

According to the present invention, the condition for removing the $R^4$ group may be in the presence of an acid. The acid may be an organic or inorganic acid, e.g., HCl, trifluoroacetic acid or an aqueous solution of any of the aforesaid, e.g. 80% aqueous trifluoroacetic acid solution.

The present invention further provides the compound of following formula (XI) and a preparation method thereof, wherein the preparation method comprises reacting the compound of formula (X) with a Wittig reagent or through the HWE (Horner-Wadsworth-Emmons) reaction, resulting in the compound of formula (XI):

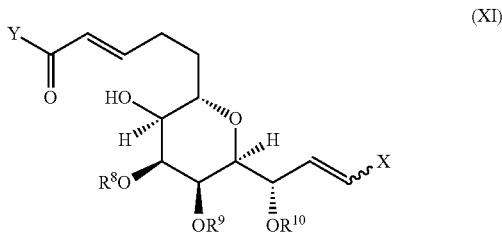

(XI)

wherein $R^8$, $R^9$, $R^{10}$, X are independently defined as described above;

Y may be an alkoxy unsubstituted or optionally substituted with one or more $R^a$.

According to the present invention, the Wittig reagent may be Y—C(O)CH=PPh$_3$;

According to embodiments of the present invention, the HWE reaction may be performed by reacting the compound of formula (X) with Y—C(O)CH$_2$P(O)(OR$^{14}$)$_2$ in the presence of an alkali, yielding the compound of formula (XI), in which each of $R^{14}$ is the same or different and is independently selected from alkyl groups. As an example, Y—C(O)CH=P(R$^{14}$)$_3$ is methyl (triphenylphosphoranylidene)acetate.

The present invention further provides a compound of following formula (XII) and a preparation method thereof, wherein the preparation method comprises allowing the compound of formula (XI) to undergo the Michael addition reaction and remove the hydroxyl protecting group, resulting in the compound of formula (XII):

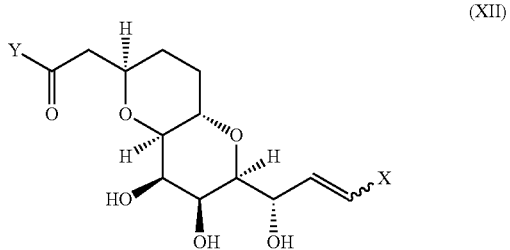

(XII)

wherein X, Y are independently defined as described above.

According to the present invention, the method of preparing the compound of formula (XII) comprises: reacting the compound of formula (XI) with a solution of Triton B in methanol, whereby the compound is subjected to the Michael addition reaction and the hydroxyl protecting group is removed, to obtain a compound of formula (XII);

As an example, the solution of Triton B in methanol is the solution of 40% Triton B in methanol;

Preferably, the molar ratio of Triton B to the compound of formula (XI) may be (5-10):1, e.g., 6:1;

The present invention further provides the compound of following formula (XIII) and a preparation method thereof, wherein the preparation method comprises reacting the compound of formula (XII) with a hydroxyl-protecting agent, e.g., silane compounds, resulting in the compound of formula (XIII):

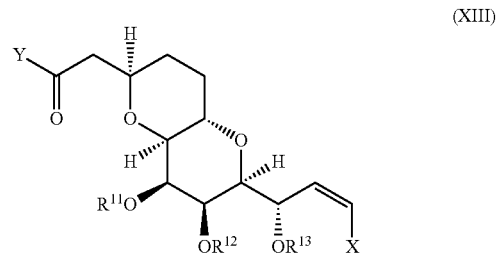

(XIII)

wherein X, Y are independently defined as described above;

$R^{11}$, $R^{12}$ and $R^{13}$ are the same or different and selected independently of one another from the group consisting of hydroxyl protecting groups.

According to embodiments of the present invention, at least one, two or any one of $R^8$, $R^9$, $R^{10}$ is different from $R^{11}$, $R^{12}$, $R^{13}$. As an example, $R^8$, $R^9$, $R^{10}$ may be selected from acetyl; and $R^{11}$, $R^{12}$, $R^{13}$ may be selected from TBS.

According to embodiments of the present invention, silane compounds may be selected from TBSC1, TBSOTf, TMSC1, TMSOTf, TESC1, TESOTf, TBDPSC1, TIPSC1, or trimethylsilyl imidazol.

According to the present invention, reaction for conversion from the compound (XII) to the compound (XIII) may be performed in dichloromethane in the presence of 2,6-dimethylpuridine and TBSOTf; wherein the molar ratio of 2,6-dimethylpuridine to the compound (XII) may be (3-8):1, such as 6:1; and the molar ratio of TBSOTf to compound (XII) may be (3-6):1, such as 4.5:1.

As an alternative, preparation of the compound of formula (XIII) from the compound of formula (V-1) may be accomplished with the following method:

removing the hydroxyl protecting group $R^4$ from the compound of formula (V-1), to synthesize a compound (V-2) subsequently, the compound (V-2) is subjected to stepwise or concurrent hydroxyl-protection, to obtain a compound (V-3); the compound (V-3) is then subjected to removing of the protecting group $R^6$ to generate a compound (V-4); and the compound (V-4) is oxidized to generate an aldehyde (V-5), subsequently yielding the compound (XIII):

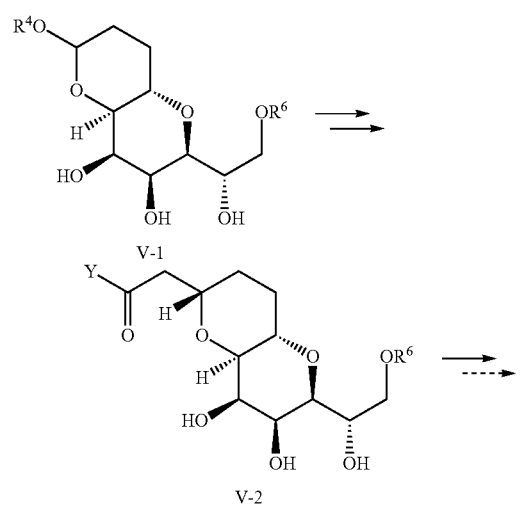

V-1

V-2

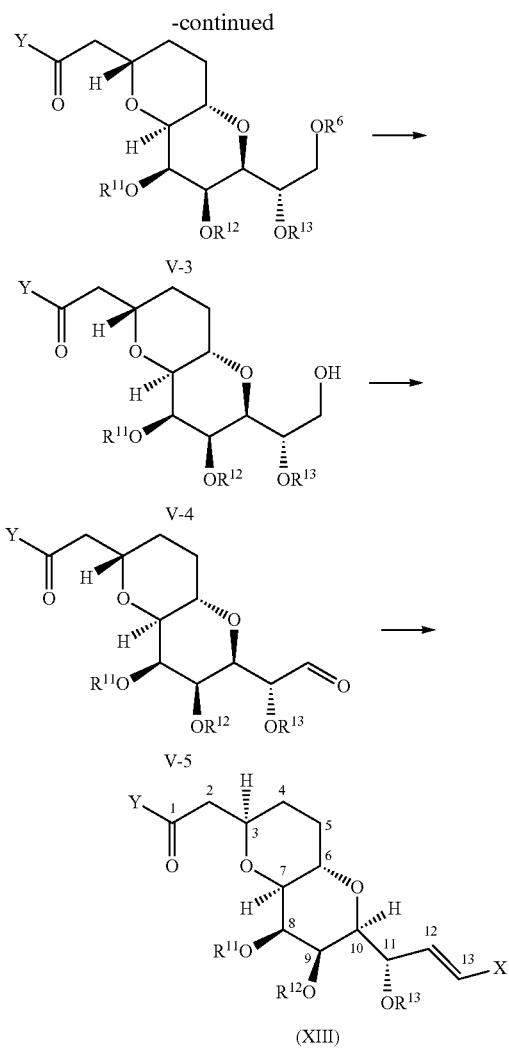

According to embodiments of the present invention, the compound (V-1) may be converted to the compound (V-2), for example, by a method similar to the aforesaid method of converting the compound (X) to the compound (XII). For example, the compound (V-1) is subjected to removing of the $R^4$ group under the aforesaid condition for removing the $R^4$ group, then reacted with the above-mentioned Wittig reagent or through the HWE (Horner-Wadsworth-Emmons) reaction, furthermore undergoes the above-mentioned Michael addition reaction and hydroxyl removing, yielding the compound (V-2);

Preferably, the compound (V-2) may be converted to the compound (V-3) by a method similar to the method of converting the compound (XII) to the compound (XIII). For example, the compound (V-2) is reacted with the hydroxyl-protecting agent as described above, such as silane compounds, yielding the compound (V-3).

Preferably, the compound (V-3) may be converted to the compound (V-4) by a method similar to the method of converting the compound (VI) to the compound (VII). For example, the compound of formula (V-3) is reacted under the above-mentioned condition for removing the $R^6$ group, resulting in the compound of formula (V-4).

Preferably, the compound (V-4) may be converted to the compound (V-5) by a method similar to the method of converting the compound (VII) to the compound (VIII). For example, the compound of formula (V-4) is reacted in the presence of the aforesaid oxidizing agent, resulting in the compound of formula (V-5).

Preferably, the compound (V-5) may be converted to the compound (XIII), for example, by a method similar to the aforesaid method of converting the compound (VIII) to the compound (IX). For example, the compound (V-5) is reacted with $CHX_3$ in the presence of chromium halide, yielding the compound (XIII).

According to one or more of the methods of the present invention, the methods may be performed optionally in the presence of a solvent.

According to one or more of the methods of the present invention, the methods may be performed optionally in an inert atmosphere.

The present invention further provides a method for preparing Halichondrin B, Eribulin, analogues thereof or C1-C13 moieties thereof, comprising use of any of the compounds mentioned above in the formulas (I) to (XIII) and/or use of one or more of the above-mentioned preparation methods.

The present invention further provides use of any of the compounds mentioned above in the formulas (I) to (XIII) in preparation of Halichondrin B, Eribulin, analogues thereof or C1-C13 moieties thereof.

Terms and Definitions

Unless defined otherwise, all technical and scientific terms used herein have the same meaning as commonly understood by those skilled in the art to which the subject matter of the claims pertain. Unless specified otherwise, the full contents of all patents, patent applications, publications cited herein are hereby incorporated herein by reference in their entirety.

When a numerical range documented in the present application the specification and claims is understood as an "integer", it should be understood to document two end points of the range and each of the integers within the range. For example, "integer from 1 to 10" should be understood to document each of the integers of 0, 1, 2, 3, 4, 5, 6, 7, 8, 9 and 10. When the numerical range is understood as a "number", it should be understood to document two end points of the range and each of the integers within the range. For example, "integer from 1 to 10" should be understood to not only document each of the integers of 1, 2, 3, 4, 5, 6, 7, 8, 9 and 10, but also document at least the sum of the each of the integers thereof and 0.1, 0.2, 0.3, 0.4, 0.5, 0.6, 0.7, 0.8, 0.9, respectively.

The term "alkyl" should be understood to preferably indicate saturated, straight- or branched-chain monovalent hydrocarbyl groups having 1-40 carbon atoms, preferably $C_{1-10}$ alkyl. "$C_{1-10}$ alkyl" should be understood to preferably indicate saturated, straight- or branched-chain monovalent hydrocarbyl groups having 1, 2, 3, 4, 5, 6, 7, 8, 9 or 10 carbon atoms. For example, the alkyl is methyl, ethyl, propyl, butyl, pentyl, hexyl, iso-propyl, iso-butyl, sec-butyl, tertiary-butyl, iso-pentyl, 2-methylbutyl, 1-methylbutyl, 1-ethylpropyl, 1,2-dimethylpropyl, neopentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl or 1,2-dimethylbutyl and so forth or isoforms thereof. In particular, the groups have 1, 2, 3, 4, 5, 6 carbon atoms ("$C_{1-6}$ alkyl"), e.g., methyl, ethyl, propyl, butyl, iso-propyl, iso-butyl, sec-butyl, tertiary-butyl, and more particularly have 1, 2 or 3 carbon atoms ("$C_{1-3}$ alkyl"), e.g., methyl, ethyl, n-propyl or iso-propyl.

The term "alkenyl" should be understood to preferably indicate straight- or branched-chain monovalent hydrocarbyl groups comprising one or more double bonds and having 2-40 carbon atoms, preferably "$C_{2-10}$ alkenyl". "$C_{2-10}$ alkenyl" should be understood to preferably indicate straight- or branched-chain monovalent hydrocarbyl groups comprising one or more double bonds and having 2, 3, 4, 5, 6, 7, 8, 9 or 10 carbon atoms, particularly 2 or 3 carbon atoms ("$C_{2-3}$ alkenyl"). In case that the alkenyl comprises more than one double bond, the double bond may be separated from each other or conjugated. For example, the alkenyl is vinyl, allyl, (E)-2-methylvinyl, (Z)-2-methylvinyl, (E)-but-2-enyl, (Z)-but-2-enyl, (E)-but-1-enyl, (Z)-but-1-enyl, pent-4-enyl, (E)-pent-3-enyl, (Z)-pent-3-enyl, (E)-pent-2-enyl, (Z)-pent-2-enyl, (E)-pent-1-enyl, (Z)-pent-1-enyl, hex-5-enyl, (E)-hex-4-enyl, (Z)-hex-4-enyl, (E)-hex-3-enyl, (Z)-hex-3-enyl, (E)-hex-2-enyl, (Z)-hex-2-enyl, (E)-hex-1-enyl, (Z)-hex-1-enyl, isopropenyl, 2-methylprop-2-enyl, 1-methylprop-2-enyl, 2-methylprop-1-enyl, (E)-1-methylprop-1-enyl, (Z)-1-methylprop-1-enyl, 3-methylbut-3-enyl, 2-methylbut-3-enyl, 1-methylbut-3-enyl, 3-methylbut-2-enyl, (E)-2-methylbut-2-enyl, (Z)-2-methylbut-2-enyl, (E)-1-methylbut-2-enyl, (Z)-1-methylbut-2-enyl, (E)-3-methylbut-1-enyl, (Z)-3-methylbut-1-enyl, (E)-2-Methylbut-1-enyl, (Z)-2-methylbut-1-enyl, (E)-1-methylbut-1-enyl, (Z)-1-methylbut-1-enyl, 1,1-dimethylprop-2-enyl, 1-ethylprop-1-enyl, 1-propylvinyl, 1-isopropylvinyl.

The term "cycloalkyl" should be understood to indicate saturated, monovalent, monocyclic or bicyclic hydrocarbon rings having the 3-20 carbon atoms, preferably "$C_{3-10}$ cycloalkyl". The term "$C_{3-10}$ cycloalkyl" should be understood to indicate saturated, monovalent monocyclic or bicyclic hydrocarbon rings having the 3, 4, 5, 6, 7, 8, 9 or 10 carbon atoms. The $C_{3-10}$ cycloalkyl may be a monocyclic ring hydrocarbyl groups, such as cylcopropyl, cyclobutyl, cyclopentyl, cyclohexyl, cycloheptyl, cyclooctyl, cyclononyl or cyclodecanyl, or bicyclic hydrocarbyl groups, such as decalin ring.

The term "heterocyclyl" is intended to denote saturated, monovalent monocyclic or bicyclic hydrocarbon rings comprising 1-5 heteroatoms independently selected from N, O and S, preferably "3-10 membered heterocyclyl". The term "3-10-membered heterocyclyl" is intended to denote saturated, monovalent monocyclic or bicyclic hydrocarbon rings comprising 1-5, preferably 1-3 heteroatoms independently selected from N, O and S. The heterocyclyl may be connected to the rest of the molecule through any one of the carbon atoms or the nitrogen atom (if present). In particular, the heterocyclyl may include, but is not be limited to: 4-membered rings, such as azetidinyl, oxetanyl; 5-membered rings, such as tetrahydrofuranyl, dioxolyl, pyrrolidinyl, imidazolidinyl, pyrazolidinyl, pyrrolinyl; or 6-membered rings, such as tetrahydropyranyl, piperidinyl, morpholinyl, dithianyl, thiomorpholinyl, piperazinyl or trithianyl; or 7-membered rings, such as diazepanyl. Optionally, the heterocyclyl may be benzo-fused. The heterocyclyl may be an bicyclic, e.g., but is not limited to 5,5-membered rings, such as hexahydrcyclopenta[c]pyrrole-2(1H)-yl ring, or 5,6-membered bicyclic rings, such as hexahydropyrrolo[1,2-a]pyrazin-2(1H)-yl ring. A ring containing nitrogen atom may be an partially unsaturated, that is, it may comprise one or more double bonds, e.g., but is not limited to 2,5-dihydro-1H-pyrrolyl, 4H-[1,3,4]thiadiazinyl, 4,5-dihydrooxazolyl or 4H-[1,4] thiazinyl, or, may be an benzo-fused, e.g., but is not limited to dihydroisoquinolinyl, 1,3-benzoxazolyl, 1,3-benzodioxolyl. According to the present invention, the heterocyclyl is non-aromatic.

The term "aryl" should be understood to preferably indicate monovalent, aromatic or partially aromatic, mono-, bi- or tri-cyclic hydrocarbon rings having 6-20 carbon atoms, preferably "$C_{6-14}$ aryl". The term "$C_{6-14}$ aryl" should be understood to preferably indicate monovalent, aromatic or partially aromatic, mono-, bi- or tri-cyclic hydrocarbon rings having 6, 7, 8, 9, 10, 11, 12, 13 or 14 carbon atoms ("$C_{6-14}$ aryl"), in particular rings having 6 carbon atoms ("$C_6$ aryl"), e.g., phenyl or biphenyl, or rings having 9 carbon atoms ("$C_9$ aryl"), e.g., indanyl or indenyl, or rings having 10 carbon atoms ("$C_{10}$ aryl"), e.g., tetrahydronaphthalenyl, dihydronaphthalenyl or naphthalenyl, or rings having 13 carbon atoms ("$C_{13}$ aryl"), e.g., fluorenyl, or rings having 14 carbon atoms ("$C_{14}$ aryl"), e.g., anthracenyl.

The term "heteroaryl" should be understood to include a monovalent, mono-, bi- or tri-cyclic aromatic ring system which has 5-20 ring atoms and comprises 1-5 heteroatoms independently selected from N, O and S, e.g., "5-14-membered heteroaryl". The term "5-14-membered heteroaryl" should be understood to include a monovalent, mono-, bi- or tri-cyclic aromatic ring system which has 5, 6, 7, 8, 9, 10, 11, 12, 13 or 14 ring atoms, in particular 5 or 6 or 9 or 10 carbon atoms, and comprise 1-5, preferably 1-3 heteroatoms independently selected from N, O and S; and, additionally in each case is the ring system may be benzo-fused. In particular, heteroaryl is selected from thienyl, furanyl, pyrrolyl, oxazolyl, thiazolyl, imidazolyl, pyrazolyl, isoxazollyl, isothiazolyl, oxadiazolyl, triazolyl radical, thiadiazolyl, thia-4H-pyrazolyl and so forth as well as benzo derivatives thereof, e.g., benzofuranyl, benzothienyl, benzoxazolyl, benzisoxazolyl, benzoimidazolyl, benzotriazolyl, indazolyl, indolyl, isoindolyl and so forth; or pyridinyl, pyridazinyl, pyrimidinyl, pyrazinyl, triazinyl and so forth, as well as benzo derivatives thereof, e.g., quinolinyl, quinazolinyl, isochinolinyl and so forth; or azocinyl, indolizinyl, purinyl and so forth as well as benzo derivatives thereof; or cinnolinyl, phthalazinyl, quinazolinyl, quinoxalinyl, naphthyridinyl, pteridinyl, carbazolyl, acridinyl, phenazinyl, phenothiazinyl, phenoxazinyl and so forth.

Unless otherwise specified, heterocyclyl, heteroaryl or heteroarylene comprises all possible isomeric forms, e.g., positional isomers thereof. Hence, for a few illustrative nonlimiting examples, pyridinyl or pyridinylene comprises pyridine-2-yl, pyridine-2-ylene, pyridin-3-yl, pyridin-3-ylene, pyridine-4-yl and pyridine-4-ylene; thienyl, or thienylene comprises thiophen-2-yl, thiophen-2-ylene, thiophene-3-yl and thiophene-3-ylene.

The above-mentioned definition for the term "alkyl", such as "$C_{1-40}$ alkyl", is applicable also to other terms comprising the aforesaid term, e.g., the terms "alkoxy" and so forth. Likewise, the above-mentioned definitions for the terms "alkenyl", "alkinyl", "cycloalkyl", "heterocyclic", "aryl" and "heteroaryl" are applicable correspondingly to other terms comprising the aforesaid terms.

The "hydroxyl protecting group" set forth in the present invention is intended to denote any group which is able to protect the oxygen atom connected to the group from reacting or bond-forming. These hydroxyl protecting groups are known in the art. Exemplary hydroxyl protecting groups include, but are not limited to: acyl, ester, carbonate, carbamate, sulfonate and ether groups. In the exemplary ester hydroxyl protecting group, the group bonded with carbonyl side through a chemical bond include: $C_1$-12 alkyl (e.g., $C_{1-8}$, $C_{1-6}$, $C_{1-4}$, $C_{2-7}$, $C_{3-12}$ and $C_{3-6}$ alkyl), $C_{2-12}$ alkenyl (e.g., $C_{2-8}$, $C_{2-6}$, $C_{214}$, $C_{3-12}$ and $C_{3-6}$ alkenyl), carbocyclic $C_{6-20}$ aryl (e.g., $C_{6-15}$, $C_{6-10}$, $C_{8-20}$ and $C_{8-15}$ aryl), monocyclic $C_{1-6}$ heteroaryl (e.g., $C_{1-4}$ and $C_{2-6}$ heteroaryl), $C_{4-19}$ heteroaryl (e.g., $C_{4-10}$ heteroaryl), $(C_{6-15})$aryl$(C_{1-6})$alkyl, $(C_{4-19})$heteroaryl$(C_{1-6})$alkyl or $(C_{1-6})$heteroaryl$(C_{1-6})$alky. Specific examples of acyl for ester group include formyl, phenylcarbonylformyl, acetyl (e.g., unsubstituted acetyl or chloroacetyl, trifluoroacetyl, methoxyacetyl, tripentylmethoxyacetyl and p-chlorophenoxyacetyl), 3-phenyl propionyl, 4-oxovaleryl, 4,4-(ethylenedisulfide)valeryl, pivaloyl (Piv), vinylpivaloyl, crotonyl, 4-methoxycrotonyl, napthoyl (e.g., 1- or 2-napthoyl) and phenylcarbonyl (e.g., unsubstituted or substituted, e.g., p-methoxyphenylcarbonyl, phthaloyl (including salts, e.g., triethylamine salt and potassium salt), p-bromobenzoyl and 2,4,6-trimyethylphenylcarbonyl).

As defined herein, any heteroaryl present in the ester group may have 1-4 heteroatoms independently selected from O, N and S.

In the exemplary carbonate-based hydroxyl protecting group, R is $C_{1-12}$ alkyl (e.g., $C_{1-8}$, $C_{1-6}$, $C_{1-4}$, $C_{2-7}$, $C_{3-12}$ and $C_{3-6}$ alkyl), $C_{2-12}$ alkenyl (e.g., $C_{2-8}$, $C_{2-6}$, $C_{2-4}$, $C_{3-12}$ and $C_{3-6}$ alkenyl), carbocyclic $C_{6-20}$ aryl (e.g., $C_{6-15}$, $C_{6-10}$, $C_{8-20}$ and $C_{8-15}$ aryl), monocyclic $C_{1-6}$ heteroaryl (e.g., $C_{1-4}$ and $C_{2-6}$ heteroaryl), $C_{4-19}$ heteroaryl (e.g., $C_{4-10}$ heteroaryl), $(C_{6-15})$aryl$(C_{1-6})$alkyl, $(C_{4-19})$heteroaryl$(C_{1-6})$alkyl or $(C_{1-6})$ heteroaryl $(C_{1-6})$alky. Specific examples include, the carbonate of: methyl, 9-fluorenylmethyl, ethyl, 2,2,2-trichloroethyl, 2-(trimethylsilyl)ethyl, 2-(benzenesulfonyl)ethyl, vinyl, allyl, t-butyl, p-nitrobenzyl and benzyl.

As defined herein, any heteroaryl present in the carbonate group has 1-4 heteroatoms independently selected from O, N and S.

In the exemplary carbamate-based hydroxyl protecting group, the hydrogen atom on the amino can be substituted with the following groups: $C_{1-12}$ alkyl (e.g., $C_{1-8}$, $C_{1-6}$, $C_{1-4}$, $C_{2-7}$, $C_{3-12}$ and $C_{3-6}$ alkyl), $C_{2-12}$ alkenyl (e.g., $C_{2-8}$, $C_{2-6}$, $C_{2-4}$, $C_{3-12}$ and $C_{3-6}$ alkenyl), carbocyclic $C_{6-20}$ aryl (e.g., $C_{6-15}$, $C_{6-10}$, $C_{8-20}$ and $C_{2-12}$ aryl), monocyclic $C_{1-6}$ heteroaryl (e.g., $C_{1-4}$ and $C_{2-6}$ heteroaryl), $C_{4-19}$ heteroaryl (e.g., $C_{4-10}$ heteroaryl), $(C_{6-15})$aryl$(C_{1-6})$alkyl, $(C_{4-19})$heteroaryl $(C_{1-6})$alkyl or $(C_{1-6})$heteroaryl $(C_{1-6})$alky. Specific examples include carbamate group of N-phenyl and N-methyl-N-(o-nitrophenyl).

As defined herein, any heteroaryl present in the carbamate group may have 1-4 heteroatoms independently selected from O, N and S.

The exemplary ether-based hydroxyl protecting group includes $C_{1-12}$ alkyl (e.g., $C_{1-8}$, $C_{1-6}$, $C_{1-4}$, $C_{2-7}$, $C_{3-12}$ and $C_{3-6}$ alkyl), $C_{2-12}$ alkenyl (e.g., $C_{2-8}$, $C_{2-6}$, $C_{2-4}$, $C_{3-12}$ and $C_{3-6}$ alkenyl), $(C_{6-15})$aryl$(C_{1-6})$alkyl, $(C_{4-19})$heteroaryl$(C_{1-6})$ alkyl, $(C_{1-6})$heteroaryl$(C_{1-6})$alkyl, $(C_{1-6})$alkoxy$(C_{1-6})$alkyl, $(C_{1-6})$alkylsulfanyl$(C_{1-6})$alkyl, $(C_{6-10})$aryl $(C_{1-6})$alkoxy $(C_{1-6})$alkyl and silyl groups (e.g., tris$(C_{1-6}$ alkyl)silyl, tris $(C_{6-10}$ aryl or $C_{1-6}$ heteroaryl)silyl, bis$(C_{6-10}$ aryl or $C_{1-6}$ heteroaryl)$(C_{1-6}$ alkyl)silyl and $(C_{6-10}$ aryl or $C_{1-6}$ heteroaryl)bis$(C_{1-6}$ alkyl)silyl). Specific examples of alkyl ether group include methyl and t-butyl, and the specific example of alkenyl ether group is allyl. Ether-based hydroxyl protecting groups can be used to protect carboxyl groups (for example, $C_{1-12}$ alkyl (e.g., $C_{1-8}$, $C_{1-6}$, $C_{1-4}$, $C_{2-7}$, $C_{3-12}$ and $C_{3-6}$ alkyl), $(C_{6-15})$aryl$(C_{1-6})$alkyl, $(C_{1-6})$alkoxy$(C_{1-6})$alkyl, $(C_{1-6})$alkylthio$(C_{1-6})$alkyl, or $(C_6$-m)aryl$(C_{1-6})$alkoxy$(C_{1-6})$ alkyl). The examples of alkoxyalkyl and alkylsulfanylalkyl useable as the ether-based hydroxyl protecting group include methoxymethyl, methylthiomethyl, (2-methoxyethoxy)methyl and β-(trimethylsilyl) ethoxymethyl. The examples of arylalkyl useable as the ether-based hydroxyl protecting group include benzyl, p-methoxybenzyl (MPM), 3,4-dimethoxybenzyl, tripentylmethyl (trityl), o-nitrobenzyl, p-nitrobenzyl, p-halobenzyl, 2,6-dichlorobenzyl, p-cyanobenzyl, naphthalenylmethyl and 2- and 4-pyridylmethyl. Specific examples of silylether group include ether groups of trimethylsilyl (TMS), triethylsilyl(TES), t-butyldimethylsilyl (TBS), t-butyldiphenylsilyl (TBDPS), triisopropyl silyl (TIPS) and triphenylsilyl (TPS). Example of arylalkyloxyalkylether group is benzyloxymethylether group.

As defined herein, any heteroaryl present in the ether group has 1~4 heteroatoms independently selected from O, N and S.

Vicinal diols or 1,3-diols can be protected with a diol protecting group (e.g., to generate "protected cyclic diols"), for example, diol protecting groups being acetals (e.g., containing $C_{1-6}$ alkylidene), ketals (e.g., containing $C_{3-6}$ alkylidene or $C_{3-6}$ cycloalkyl), cyclic silylene groups, cyclic carbonate groups and cyclic boronate ester groups. Examples of acetals and ketals include methylidene-dioxo group, ethylidene-dioxo group, benzylene-dioxo group, isopropylene-dioxo group, cyclohexylene-dioxo group and cyclopentylene-dioxo group. The example of cyclic silylene group is bis-t-butyl silylene group. Another diol protecting agent is 1,1,3,3-tetraisopropylsiloxane diyl. Examples of cyclic boronate ester groups include boronate ester groups of methyl, ethyl, phenyl and 2,6-diacetamidophenyl. Protecting groups may be substituted, as is known in the art. For example, aryl and arylalkyl groups (e.g., phenyl, benzyl, naphthalenyl or pyridinyl) may be substituted with $C_{1-6}$ alkyl, $C_{1-6}$ alkoxy, nitro, cyano, carboxylate or halo. Alkyl (e.g., methyl, ethyl, iso-propyl, n-propyl, t-butyl, n-butyl and sec-butyl) and alkenyl (e.g., vinyl and allyl) can also be substituted with oxo, arylsufonyl, halo and trialkylsilyl.

A "hydroxyl protecting group comprising less than 6 carbon atoms" described in the present invention is not intended to define the hydroxyl protecting group as a substituent group comprising carbon atoms exclusively. It should be understood that the "hydroxyl protecting group comprising less than 6 carbon atoms" may comprise other atoms above-mentioned in addition to the carbon atom e.g., oxygen atom, nitrogen atom, silicon atom and so forth. For example, the "hydroxyl protecting group comprising less than 6 carbon atoms" includes, but is not limited to an ester group, carbonate group, carbamate group, sulfonate group or ether groups comprising 1, 2, 3, 4, 5, or 6 carbon atoms.

Deprotection agents for the hydroxyl protecting group are those which can react with the compounds have the protected hydroxyl so as to provide the de-protected hydroxyl group. Deprotection agents for the hydroxyl protecting group and the condition for deprotection reaction may be those known in the art. In a nonlimiting example, the hydroxyl masked as a silyl ether ay be demasked by reacting with a fluoride source (e.g., a fluoride salt, e.g., KF or TBAF). Alternatively, the hydroxyl protected as a TMS or TES ether may be deprotected by reacting with a Bronsted acid (e.g., a carboxylic acid). In another nonlimiting example, the hydroxyl protected as an ester ay be deprotected by reacting with a $C_{1-6}$ alkoxide (e.g., alkaline metal $C_{1-6}$ alkoxide or alkaline cart metal $C_{1-6}$ alkoxide). In a further nonlimiting example, the hydroxyl protected as an arylalkyl ether (e.g., 1-aryl alk-1-yl ether) may be deprotected using a reduction reaction (e.g., with Pd/C and $H_2$, or with Na/$NH_3$). Alternatively, the hydroxyl protected as an alkoxyarylalkyl ether (e.g., MPM ether) ay be deprotected by reacting with 2,3-dichloro-5,6-dicyano-1,4-benzoquinone (DDQ). In a further nonlimiting example, the hydroxyl protected as an alkoxyalkyl ether (e.g., 1-alkoxyalk-1-yl) or THP ether may be deprotected by reacting with a Bronsted acid. The protected cyclic diols (e.g., acetals or ketals (e.g., 2-alkyl-1,3-dioxolane, 2,2-dialkyl-1,3-dioxolane, 2-alkyl-1,3-dioxane or 2,2-dialkyl-1,3-dioxane)) may be deprotected by reacting with a Bronsted acid (e.g., a carboxylic acid).

An alkali described in the present invention may be organic bases, inorganic bases or mixtures thereof, for example, selected from the carbonate salts or hydrogen carbonate salts of alkaline metal or alkaline earth, e.g., lithium carbonate, sodium carbonate, potassium carbonate, calcium carbonate, cesium carbonate, sodium bicarbonate, potassium hydrogen carbonate, calcium hydrogen carbonate; alkoxides of alkaline metal, e.g., sodium tert-butylate or potassium tert-butylate; organolithium compounds such as butyllithium or phenyllithium; hydrides of alkaline metal, e.g., sodium hydride or potassium hydride; amides, e.g., lithium bis(trimethylsilyl)amide, potassium bis(trimethylsilyl)amide or lithium diisopropylamide (LDA); organic amines, e.g., triethylamine, N-methylmorpholine, piperidine, N-methylpiperidin, N,N-diisopropylethylamine, 1,5-diazabicyclo[4.3.0]non-5-ene (DBN), 1,8-diazabicyclo[5.4.0]dec-7-ene (DBU), pyridine or 4-dimethylaminopyridine (DMAP).

The acid described in the present invention, may be organic acids, inorganic acids or mixtures thereof, e.g. selected from one or more of the following: carboxylic acids, such as acetic acid or trifluoroacetic acid; sulphonic acids, e.g., methanesulfonic acid, trifluoromethanesulfonic acid or p-toluene sulfonic acid; phosphonic acid; hydrochloric acid, sulphuric acid, phosphoric acid. The acid further includes a Lewis acid. The Lewis acid may be one or more selected from $BF_3 \cdot OEt_2$, $MgCl_2$, $MgBr_2$, $ZnBr_2$, $ZnI_2$, $ZnCl_2$, $ZnSO_4$, $CuCl_2$, $CuCl$, $Cu(O_3SCF_3)_2$, $CoCl_2$, $CoI_2$, $FeI_2$, $FeCl_3$, $FeCl_2$, $FeCl_2$, $SnCl_4$, $TiCl_4$, $TiCl_3$, $MnCl_2$, $ScCl_3$, $AlCl_3$, $(i\text{-}C_4H_9)_2AlCl$, $(C_6H_5)_2AlCl$, $(C_6H_5)AlCl_2$, $ReCl_5$, $ZrCl_4$, $NbCl_5$, $VCl_3$, $CrCl_2$, $MoCl_5$, $YCl_3$, $CdCl_2$, $LaCl_3$, $Er(O_3SCF_3)_3$, $Yb(O_2CCF_3)_3$, $SmCl_3$, $B(C_6H_5)_3$, $TaCl_5$ or trimethylsilyl trifluoromethanesulfonate, the specific example of which may be one or more selected from $BF_3 \cdot OEt_2$, $MgCl_2$, $ZnCl_2$, $MgBr_2$, $ZnBr_2$, $AlCl_3$, $SnCl_4$, $TiCl_4$ or trimethylsilyl trifluoromethanesulfonate.

The solvent described in the present invention may include a mixture of one or more of the following selected from: water; keton solvents, e.g., acetone and methyl ethyl ketones; ether solvents, including acyclic ethers and cyclic ethers, e.g., ethyl ether, tetrahydrofurane, dioxane; ester solvents, e.g., ethyl acetate or butyl acetate; alkane solvents, e.g., n-hexane or n-heptane; haloalkane solvents, e.g., monochloromethane, dichloromethane, trichloromethane, carbon tetrachloride, 1,2-dichloroethane; cycloalkane solvents, e.g., cyclohexane or cycloheptane; substituted or unsubstituted arene solvents, e.g., benzene, toluene, xylene, chlorobenzene; alcohol solvents, e.g., methanol, ethanol, n-propanol, isopropanol, n-butanol or t-butanol; or other solvents, e.g., N,N-dimethylformamide (DMF), dimethyl sulphoxide (DMSO), N-methyl pyrrolidinone (NMP), acetonitrile or pyridine. Preferably, the solvent selected from an inert solvent inactive to a substrate and a catalyst of a reaction. As an example, the inert solvent may be selected from one or more of e.g., alcohol solvents (e.g., methanol, ethanol), ether solvents (e.g., ethyl ether, tetrahydrofurane, dioxane), haloalkane solvents (e.g., dichloromethane, trichloromethane, carbon tetrachloride, 1,2-dichloroethane), substituted or unsubstituted arenes (e.g., benzene, toluene, chlorobenzene), preferably alcohol solvents, mixed solvents of alcohol and water, ether solvents and/or halogenated hydrocarbon solvents.

Unless otherwise specified, the solvent in the present invention is a dry solvent.

ADVANTAGEOUS EFFECTS

Intermediates provided in the present invention are usable for preparing Halichondrin B, Eribulin, or analogues thereof, especially the key product of C1-C13 moieties, preparation methods thereof and use thereof. The starting material for the synthesis pathway of the present invention is inexpensive and readily available with sustainable source and reliable quality. Since the structural characteristics of the reactants of their self are made full use in choosing the method of constructing the chiral centers, the efficiency in the synthesis is considerably increased, the difficulty in and the risk on quality control of the product are reduced; and using a highly toxic and expensive high-valent osmium catalyst is avoided, which have the cost and environmental friendliness significantly improved.

PARTICULAR EMBODIMENTS

The above and other characteristics and advantages of the present invention will be explained and illustrated below in more details by describing the Examples of the present invention. It should be understood that the Examples below are intended to illustrate exemplarily the technical solutions of the present invention, but not to limit in any way the scope of protection of the presentinvention defined in the claims and the equivalents thereof.

Unless otherwise specified, materials and reagents herein are all the commercially available products, or can be prepared according to the state of the art by the person of skill.

It should be understood by those skilled in the art that the starting materials, reagents, intermediates, the target compounds or reaction formulas in the Examples below are all exemplary technology solutions for the compounds of general formula hereinabove or the reaction therefor, where one or more of the particular compounds or the particular reaction formulas all can be combined with generic technology solutions of the present invention, and the technology solution arising after the combination should be construed as the technology solution documented in the specification.

Unless otherwise specified, the yield in the Examples below is calculated as product purity of more than 99.5%.

EXAMPLE 1. PREPARATION OF COMPOUND 26

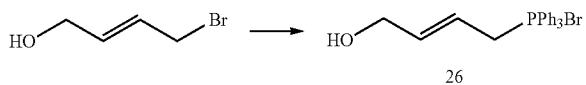

Under protection with argon gas, (E)-4-bromobut-2-en-1-ol (19 g, 0.126 mol) was dissolved in dry toluene, triphenyl phosphine (66 g, 0.25 mol) was added with stirring, heated at 60° C. to react. The reaction was completed after 3 hrs, stopped, filtered, washed with anhydrous ethyl ether, resulting in 40 g of the target compound 26, with a yield of 76%.

$^1$H NMR (400 MHz, CDCl$_3$) δ 7.78-7.65 (m, 15H), 6.03-5.98 (m, 1H), 5.66-5.61 (m, 1H), 4.49-4.44 (m, 2H), 3.99 (s, 1H), 3.94 (s, 2H).

EXAMPLE 2. PREPARATION OF COMPOUND 28

2.1 Preparation of Compound 2-03

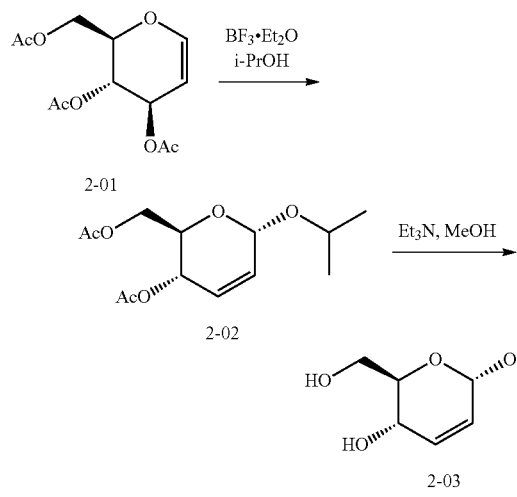

Under protection with argon gas, 2-01 (50 g, 0.18 mol) was dissolved in dry DCM (225 mL) at room temperature, isopropyl alcohol (57.5 mL) was added with stirring, and boron trifluoride ethylether (35 mL) was dropped slowly. The starting material disappeared 15 min after end of the addition and the reaction was stopped. The reactant was poured into an ice-cold aqueous sodium bicarbonate solution and stirred quickly for 15 min, extracted with DCM, dried and concentrated, obtaining 2-02. Dry methanol (1 L) was added into the resulting residue to dissolve, and water (125 mL) and triethyl amine (125 mL) were added with stirring. The resulting system was heated to 50° C. to react. After 3 hrs, the starting material disappeared and the reaction was stopped. The solvent was evaporated off and DCM was added to dissolve the residue. The resulting solution washed subsequently with water, dilute hydrogen chloride, and saturated sodium bicarbonate solution, dried and concentrated, followed by recrystallization with petroleum and ether-ethyl acetate, obtaining 25.8 g of 2-03, with a yield of 74% for the two steps.

$^1$H NMR (500 MHz. CDCl$_3$) δ 5.94 (d, J=10 Hz, 1H), 5.72 (d, J=10 Hz, 1H), 5.08 (s, 1H), 4.20 (s, 1H), 3.99-3.94 (m, 1H), 3.85 (s, 2H), 3.74-3.73 (m, 1H), 1.24 (d, J=5 Hz, 3H), 1.18 (d, J=5 Hz, 3H).

2.2 Preparation of Compound 2-04

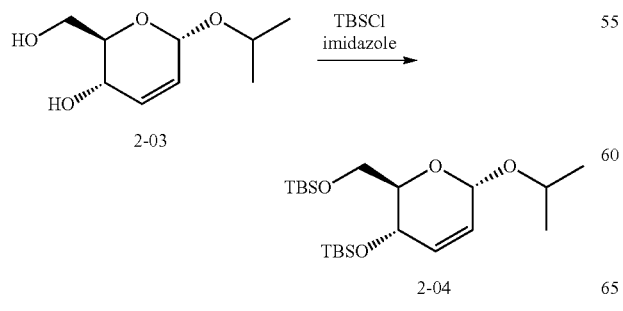

At room temperature, 2-03 (26 g, 0.138 mol) was dissolved in dry DMF (260 mL), imidazole (37.6 g, 0.55 mol) was added with stirring, TBSCl (62.2 g, 0.41 mol) was added batch wise and then the reaction system was heated to 60° C. to react. After 2 h the reaction was completed and stopped, ethyl acetate was added to dissolve. The resulting solution was sequentially washed with water and saturation sodium chloride solution, dried, and evaporated off the solvent, and separated by column chromatography, resulting in 49.5 g of the target compound 2-04, with a yield of 86%.

$^1$H NMR (400 MHz, CDCl$_3$) δ 5.82 (d, J=12 Hz, 1H), 5.64 (dt, J=4 Hz, J=12 Hz, 1H), 5.05 (s, 1H), 4.12-4.10 (m, 1H), 4.03-3.97 (m, 1H), 3.88-3.83 (m, 2H), 3.74-3.69 (m, 1H), 1.24 (d, J=5 Hz, 3H), 1.16 (d, J=5 Hz, 3H), 0.90 (s, 9H), 0.88 (s, 9H), 0.08-0.07 (m, 12H).

2.3 Preparation of Compound 2-06

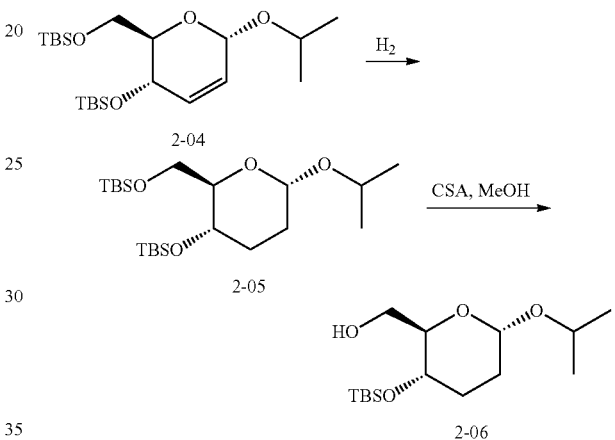

At room temperature, 2-04 (2 g, 4.8 mmol) was added into isopropanol (10 mL), 10% palladium on carbon (100 mg) was added to perform hydrogenation under atmospheric pressure. After 3 hrs the reaction was completed. The reaction was stopped and filtered. The solvent was evaporated off under the reduced pressure, obtaining Compound 2-05. Methanol and dichloromethane (32 mL, 1/1, v/v) were added to dissolve, and cooled with ice-water bath. Camphorsulfonic acid (CSA) (80 mg, 0.34 mmol) was added with stirring. After being reacted at 0° C. for 1 hour, the starting material disappeared. The reaction was stopped and washed sequentially with saturated sodium bicarbonate solution and sodium chloride solution, dried over anhydrous sodium sulphate, concentrated and separated by column chromatography, obtaining 1.28 g of the target compound 2-06, with a yield of 87%.

$^1$H NMR (500 MHz, CDCl$_3$) δ 4.83 (s, 1H), 3.90-3.85 (m, 1H), 3.78-3.73 (m, 1H), 3.68-3.55 (m, 3H), 1.84-1.69 (m, 4H), 1.21 (d, J=5 Hz, 3H), 1.12 (d, J=5 Hz, 3H), 0.87 (s, 9H), 0.06 (s, 6H).

2.4 Preparation of Compound 28

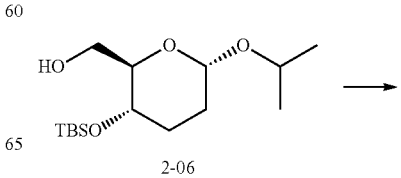

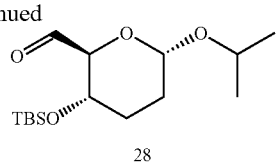

3.93-3.89 (m, 1H), 3.42-3.37 (m, 1H), 1.90-1.76 (m, 4H), 1.24 (d, J=5 Hz, 3H), 1.12 (d, J=5 Hz, 3H), 0.83 (s, 9H), 0.02 (s, 3H), −0.03 (s, 3H).

Under protection with argon gas, 2-06 (35 g; 115 mmol), DIPEA (50.9 mL), and DMSO (41.3 mL) were dissolved in dry DCM (212 mL) and cooled in an ice-water bath. Pyridine-sulphur trioxide (py.SO₃) (36.5 g, 0.23 mol) was added batch wise. After addition, the reaction proceeded for 1 hour and the starting material disappeared. DCM was added to dilute. The resulting mixture was subsequently washed with water, 0.1N HCl, saturated aqueous NaHCO₃ solution, and aqueous NaCl solution, dried, and separated by column chromatography, resulting in 34 g of the compound 28, with a yield of 97%.

$^1$H NMR (400 MHz, CDCl$_3$) δ 9.79 (s, 1H), 4.96 (s, 1H), 4.14 (d, J=8 Hz, 1H), 3.91-3.85 (m, 1H), 3.72 (dt, J=8 Hz, J=4 Hz, 1H), 1.85-1.69 (m, 4H), 1.18 (d, J=8 Hz, 3H), 1.11 (d, J=8 Hz, 3H), 0.87 (s, 9H), 0.06 (s, 3H), 0.03 (s, 3H).

EXAMPLE 3. PREPARATION OF COMPOUND 29

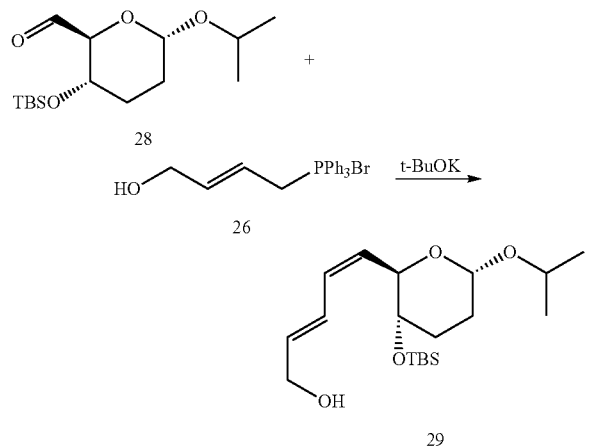

Under protection with argon gas, phosphonium 26 (15.9 g, 3.8 mmol) was dissolved in dry THF (220 mL) and chilled at −78° C. t-BuOK (4.4 g, 3.9 mmol) was added batch wise and stirred for 40 min. The reaction solution became from colorless to deep red. Then the solution of the compound 28/THF (10 g/20 mL) was dropped slowly (lasting for about 1.3 h). About 1 h after completing addition, the reaction was quenched by adding the saturated aqueous NH₄Cl solution. The resulting reaction mixture was extracted with ethyl acetate, subsequently washed with saturated NaHCO₃, NaCl solutions, dried and concentrated. Ethyl ether/n-hexane (1:2) was added. The resulting mixture was stirred quickly and filtered. The filtrate was concentrated and separated on a column (PE:EA=10:1), resulting in 9.6 g of the compound 29, with a yield of 82%.

$^1$H NMR (500 MHz, CDCl$_3$) δ 6.60 (t, J=10 Hz, 1H), 6.18 (t, J=10 Hz, 1H), 5.88-5.82 (m, 1H), 5.34 (t, J=10 Hz, 1H), 4.86 (s, 1H), 4.46 (t, J=10 Hz, 1H), 4.19 (d, J=10 Hz, 2H),

EXAMPLE 4. PREPARATION OF COMPOUND 33

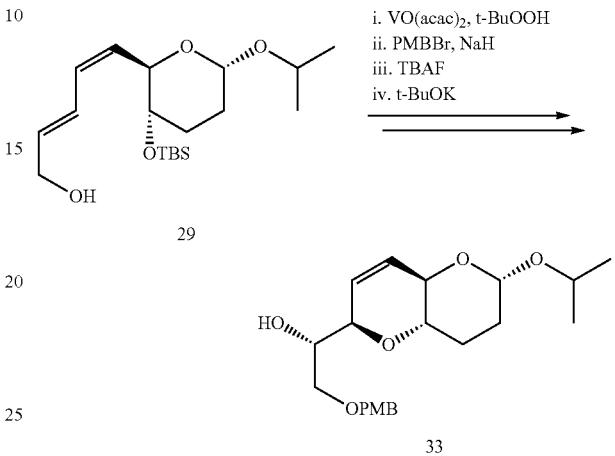

Under protection with argon gas, the compound 29 (11.5 g, 32 mmol) was dissolved in dry DCM (220 mL), VO(acac)₂ (856 mg, 3.2 mmol) was added and cooled in an ice-water bath, t-BuOOH (16.8 mL, 64.6 mmol) was dropped slowly (over 20-30 min), About 1 h after completing addition, the starting material disappeared and the reaction was quenched by adding Na₂S₂O₃H₂O. The resulting reaction mixture was extracted with DCM, washed with saturated NaHCO₃ and NaCl solutions, dried and concentrated before being dissolved in dry DMF. The resulting solution was dropped slowly into NaH/DMF (1.9 g, 48 mmol/58 mL) (at −5° C.). After completing addition, stirring proceeded for 20 min. Para-methoxybenzyl bromide (8.4 g, 42 mmol) was added and reacted at −5° C. for about 3 hrs. The reaction was quenched by adding saturated NH₄Cl solution. The resulting mixture was extracted with ethyl ether, washed with saturated NaHCO₃ and NaCl solutions, dried and concentrated. Then a solution of 1 M tetrabutylammonium fluoride in THF (64 mL) was added. After reacting at room temperature for 1 h, the starting material disappeared, methanol (105 mL) was added to dissolve, and t-BuOK (10.8 g, 96 mmol) was added batch wise. After reacting at room temperature for 2 hrs, the starting material disappeared and the reaction was stopped. Under the reduced pressure, a part of the solvent was evaporated off. The resulting mixture was extracted with ethyl acetate, washed with saturation NaCl solution, dried and concentrated, followed by column chromatography separation, resulting in 6.59 g of the compound 33, with a yield of 54%.

$^1$H NMR (400 MHz, CDCl$_3$) δ 7.26 (d, J=8 Hz, 2H), 6.88 (d, J=8 Hz, 2H), 5.94 (dd, J=40 Hz, J=12 Hz, 2H), 4.91 (s, 1H), 4.50 (s, 2H), 4.12-4.10 (m, 2H), 3.96-3.84 (m, 2H), 3.80 (s, 3H), 3.70 (dd, J=8 Hz, J=4 Hz, 1H), 3.59-3.55 (m, 1H), 3.25-3.21 (m, 1H), 2.52 (d, J=4 Hz, 1H), 1.84-1.72 (m, 4H), 1.20 (d, J=4 Hz, 3H), 1.14 (d, J=4 Hz, 3H).

EXAMPLE 5. PREPARATION OF COMPOUND 33

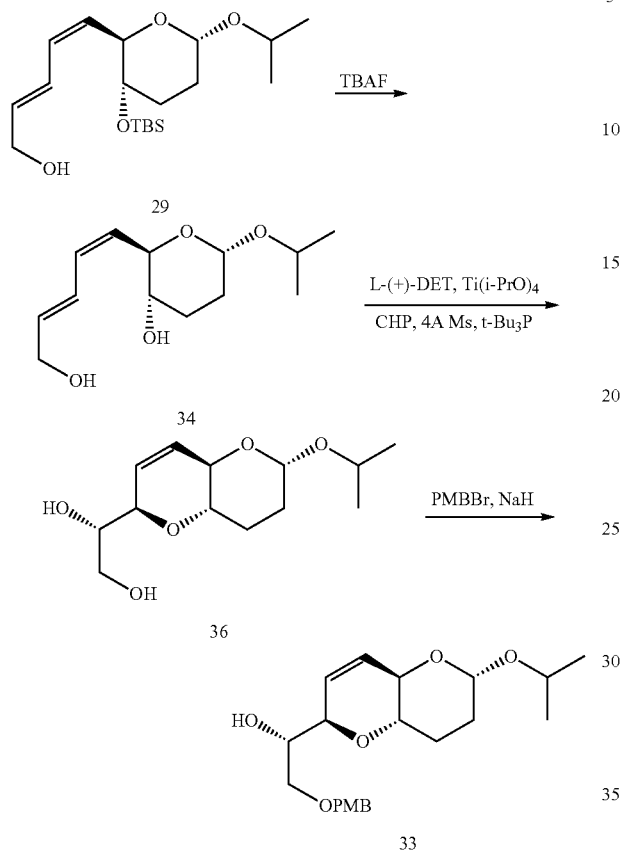

At room temperature, the compound 29 (2 g, 5.6 mmol) was dissolved in THF (10 mL) and a solution of 1 M tetrabutylammonium fluoride in THF (8.4 mL) was added with stirring. After reacting at room temperature for 1 h, the starting material disappeared and the reaction was stopped. The solvent was evaporated off under the reduced pressure, followed by separation on a column (PE:EA=1:1), resulting in 1.17 g of the compound 34, with a yield of 86%.

Under protection with argon gas, 4 Å molecular sieve (306 mg) was added to dry DCM (8 mL) and chilled at −40° C. Subsequently, L-(+)-diethyl tartarate (255 mg, 1.2 mmol) and tetraisopropoxytitanium (282 mg, 0.99 mmol) was added with stirring. After 30 min, cumene hydroperoxide (628 mg, 3.3 mmol) was added. After 30 min, the compound 34 (200 mg, 0.82 mmol) was added and warmed up to −25° C. to react over night. The starting material disappeared and the reaction was stopped. Tributylphosphine was added to quench the reaction. After stirring for 20 min aqueous L-(+)-tartaric acid solution was added and stirred sufficiently. The resulting mixture was extracted with ethyl acetate, dried and concentrated, followed by being separated by column chromatography, resulting in 142 mg of the compound 36, with a yield of 66%.

At room temperature, the compound 36 (512 mg, 1.98 mmol) was dissolved in THF (5 mL) and cooled in an ice-water bath. NaH (87 mg, 2.1 mmol) was added. After stirring for 30 min, p-methoxybenzyl bromide (436 mg, 2.1 mmol) was added. After 1 h, the starting material disappeared. The resulting reaction was separated by column chromatography, resulting in 585 mg of the compound 33, with a yield of 78%.

$^1$H NMR (400 MHz, CDCl$_3$) δ 7.26 (d, J=8 Hz, 2H), 6.88 (d, J=8 Hz, 2H), 6.00-5.87 (m, 2H), 4.91 (s, 1H), 4.50 (s, 2H), 4.12-4.10 (m, 2H), 3.96-3.84 (m, 2H), 3.80 (s, 3H), 3.70 (dd, J=8 Hz, J=4 Hz, 1H), 3.59-3.55 (m, 1H), 3.25-3.21 (m, 1H), 2.52 (d, J=4 Hz, 1H), 1.84-1.72 (m, 4H), 1.20 (d, J=4 Hz, 3H), 1.14 (d, J=4 Hz, 3H).

EXAMPLE 6. PREPARATION OF COMPOUND 38

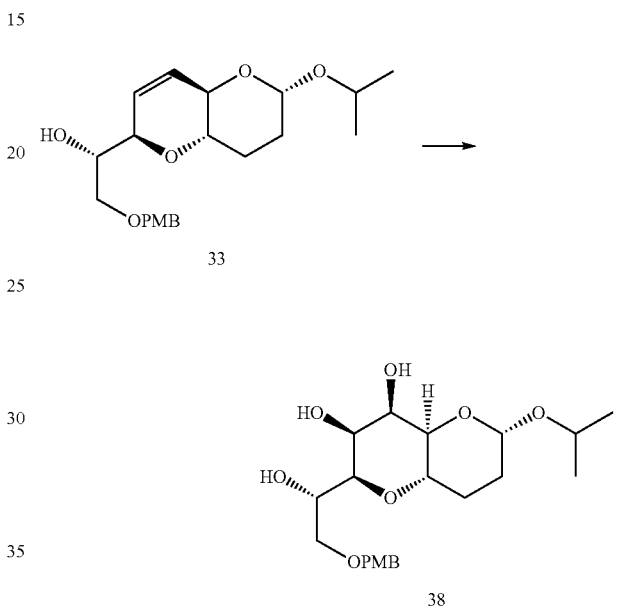

Bis(pinacolato) diboron (26.9 g, 0.106 mol) and cesium carbonate (8.6 g, 26 mmol) were added in a reaction flask in which argon gas was purged 3 times. Then, the compound 33 (10 g, 26 mmol) THF solution (55 mL), and dry methanol (18 mL) were added. After completion of the addition, the reaction was heated under protection with argon gas to reflux (at about 70° C.) over night. Then the reaction was stopped and cooled to room temperature. The solvent was evaporated off and THF (170 mL) and water (120 mL) were added to dissolve the residue. Sodium peroxoborate tetra-hydrate (30 g, 0.196 mol) was added batch wise while being cooled in an ice-water bath. After completion of the addition, the reaction was warmed up spontaneously to room temperature to proceed. After about 2 hrs, the reaction was completed, filtered, extracted with DCM, dried and concentrated; resulting in a crude. The resulting crude was separated by column chromatography, resulting in 5.6 g of the compound 38, with a yield of 50%.

$^1$H NMR (400 MHz, CDCl$_3$) δ 7.25 (d, J=8 Hz, 2H), 6.86 (d, J=8 Hz, 2H), 4.92 (s, 1H), 4.85 (t, J=8 Hz, 1H), 4.49 (s, 2H), 4.12 (s, 1H), 3.97-3.95 (m, 1H), 3.89-3.82 (m, 2H), 3.78 (s, 3H), 3.64 (dd, J=8 Hz, J=4 Hz, 1H), 3.54-3.47 (m, 3H), 1.76-1.67 (m, 4H), 1.18 (d, J=10 Hz, 3H), 1.12 (d, J=10 Hz, 3H).

EXAMPLE 7. PREPARATION OF COMPOUND 39

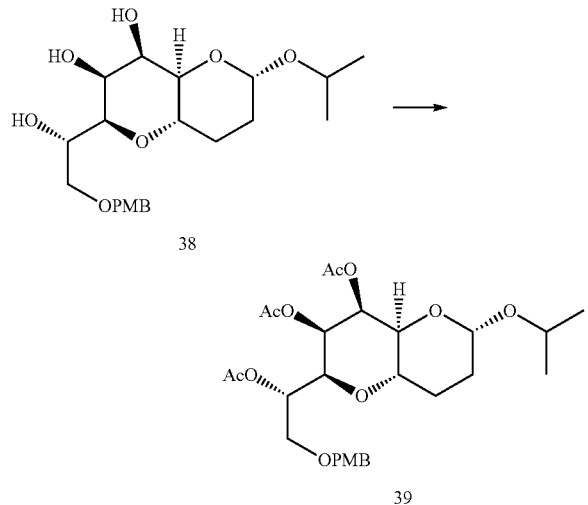

At room temperature, the compound 38 (12 g, 29 mmol) was dissolved in Py/Ac$_2$O (90 mL, v/v=1:1) and DMAP (388 mg, 3.1 mmol) was added. After completion of the addition, the system was allowed to react at room temperature for 5 hrs. The starting material disappeared and the reaction was stopped. Ethyl acetate was added to dissolve the system. The resulting solution washed with 1 N HCl, saturated NaHCO$_3$ and NaCl solutions, dried and concentrated, resulting in 14 g of the target compound 39, with a yield of 89%.

$^1$H NMR (500 MHz, CDCl$_3$) δ 7.26 (d, J=10 Hz, 2H), 6.87 (d, J=10 Hz, 2H), 6.14 (s, 1H), 5.54 (s, 1H), 5.20-5.19 (m, 1H), 4.86 (s, 1H), 4.51 (dd, J=50 Hz, J=10 Hz, 2H), 3.87-3.80 (m, 5H), 3.67-3.65 (m, 2H), 3.57-3.50 (m, 2H), 2.22 (s, 3H), 2.04 (s, 3H), 1.96 (s, 3H), 1.77-1.61 (m, 4H), 1.20 (d, J=5 Hz, 3H), 1.10 (d, J=5 Hz, 3H).

EXAMPLE 8. PREPARATION OF COMPOUND 40

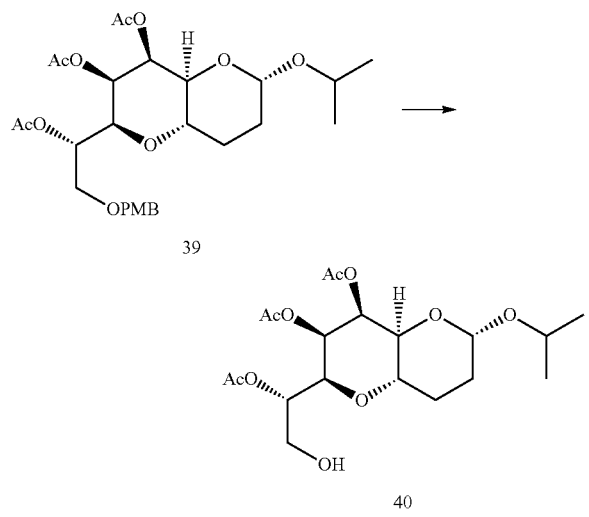

The Compound 39 (8.66 g, 16 mmol) was dissolved in a mixed solvent of DCM and H$_2$O (176 mL, DCM/H$_2$O=10/1), and the reaction was cooled in an ice-water bath, and DDQ (6.03 g, 32 mmol) was added batch wise. After completion of the addition, the reaction was warmed up spontaneously to room temperature to proceed. By being monitored by TLC, the reaction was completed after about 3 hrs. The reaction flask was cooled again in the ice-water bath and the reaction was quenched by adding the saturated NaHCO$_3$ solution and extracted with DCM two times. The organic phases were pooled and washed with saturated NaCl solution, dried and concentrated, followed by being separated by column chromatography, resulting in 6.03 g of the compound 40, with a yield of about 90%.

$^1$H NMR (500 MHz, Chloroform-d) δ 6.13-5.89 (m, 1H), 5.56 (d, J=2.9 Hz, 1H), 5.22 (dd, J=6.5, 3.0 Hz, 1H), 4.89 (s, 1H), 4.19 (dd, J=9.9, 6.4 Hz, 1H), 3.86 (dd, J=13.1, 6.6 Hz, 3H), 3.70 (dd, J=9.9, 2.9 Hz, 1H), 3.66-3.55 (m, 1H), 2.21 (s, 3H), 2.07 (s, 3H), 1.98 (s, 3H), 1.88-1.79 (m, 4H), 1.20 (d, J=6.2 Hz, 3H), 1.12 (d, J=6.1 Hz, 3H).

EXAMPLE 9. PREPARATION OF COMPOUND 33B

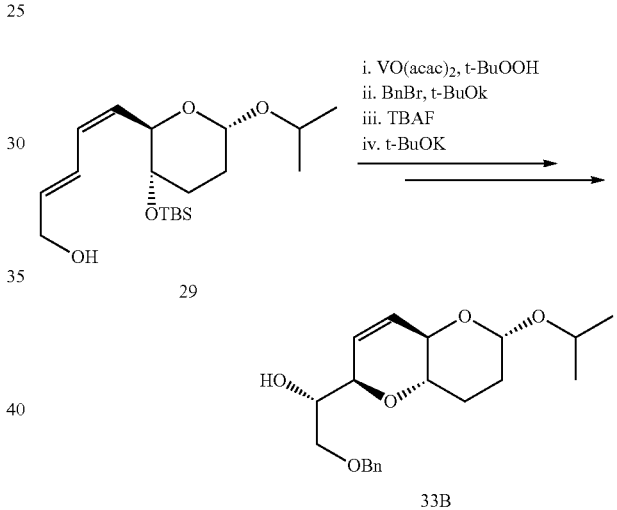

Under protection with argon gas, the compound 29 (3 g, 8.4 mmol) was dissolved in dry DCM (60 mL), VO(acac)$_2$ (223 mg, 0.84 mmol) was added and cooled in an ice-water bath, and t-BuOOH (4.1 mL, 16.8 mmol) was dropped slowly (over 20-30 min). About 1 h after completion of the addition, the starting material disappeared and the reaction was quenched by adding Na$_2$S$_2$O$_3$.H$_2$O. The resulting reaction mixture was extracted with DCM, washed with saturated NaHCO$_3$ and NaCl solutions, dried and concentrated, resulting in a crude of 4.1 g. The crude was dissolved in dry THF and, cooled in an ice-water bath. t-BuOK (1.13 g, 10.09 mmol) was added and the stirring proceeded for 20 min before benzyl bromide (1.59 g, 9.3 mmol) was added. After completion of the addition, the reaction was warmed up spontaneously to room temperature to proceed over night. The starting material disappeared. The reaction was quenched by adding the saturated NH$_4$Cl solution, extracted with ethyl ether, washed with saturated NaHCO$_3$ and NaCl solutions, dried and concentrated, resulting in a crude of 4.8 g. A solution of 1 M tetrabutylammonium fluoride in THF (17 mL) was added into the resulting crude. After 2=hrs of reaction at room temperature, the starting material disappeared. Methanol (28 mL) was added for solubilizing and t-BuOK (2.83 g, 25.2 mmol) added batch wise. After 2 hrs of reaction at room temperature, the starting material disappeared. The reaction was stopped and a part of the solvent was evaporated off under the reduced pressure. The remaining was extracted with ethyl acetate, washed with saturation NaCl solution, dried and concentrated, followed by being separated by column chromatography, resulting in 1.2 g of the compound 33B, with a yield of 40.9%.

$^1$H NMR (400 MHz, Chloroform-d) δ 7.40-7.29 (m, 5H), 6.07-5.95 (m, 1H), 5.90 (d, J=10.5 Hz, 1H), 4.92 (s, 1H), 4.58 (s, 2H), 4.31-4.07 (m, 2H), 4.02-3.83 (m, 2H), 3.74 (dd, J=9.5, 3.0 Hz, 1H), 3.61 (ddd, J=9.6, 6.4, 0.9 Hz, 1H), 3.23 (t, J=9.3 Hz, 1H), 1.90-1.70 (m, 4H), 1.21 (d, J=6.3 Hz, 3H), 1.14 (d, J=6.1 Hz, 3H).

EXAMPLE 10. PREPARATION OF COMPOUND 38B

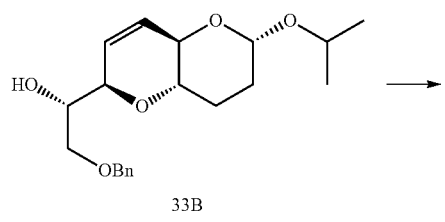

33B

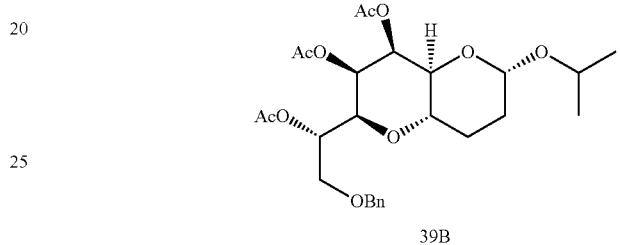

38B

Bis(pinacolato) diboron (2.74 g, 10.78 mmol) and cesium carbonate (878 mg, 2:7 mmol) were added in a reaction flask in which argon gas was purged 3 times. Then, the compound 33B (940 mg, 2.7 mmol) THF solution (6 mL), and dry methanol (1.86 mL) were added. After completion of the addition, the reaction was heated under protection with argon gas to reflux over night. Then the reaction was stopped and cooled to room temperature. The solvent was evaporated off and THF (17 mL) and water (17 mL) were added to dissolve the residue. Sodium peroxoborate tetra-hydrate (6.6 g, 43 mmol) was added batch wise while being cooled in an ice-water bath. After completion of the addition, the reaction was warmed up spontaneously to room temperature to proceed. After about 2 hrs, the reaction was completed, filtered, extracted with DCM, dried and concentrated, resulting in a crude. The resulting crude was separated by column chromatography, resulting in 544 mg of the compound 38B, with a yield of 52.7%.

$^1$H NMR (500 MHz, Chloroform-d) δ 7.38-7.19 (m, 5H), 5.17-4.75 (m, 2H), 4.57 (m, 2H), 4.45-4.03 (m, 2H), 4.01-3.81 (m, 3H), 3.79-3.39 (m, 3H), 1.71 (m, 4H), 1.18 (d, J=6.2 Hz, 3H), 1.12 (d, J=6.1 Hz, 3H).

EXAMPLE 11. PREPARATION OF COMPOUND 39

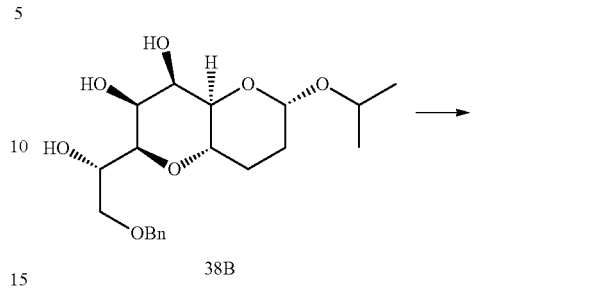

38B

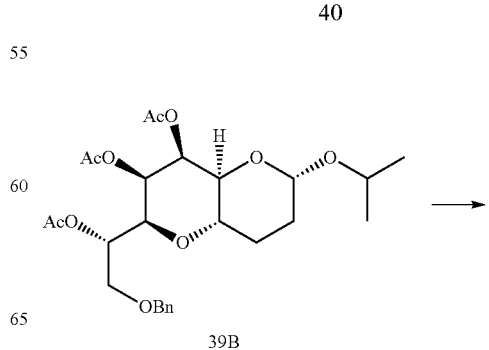

39B

At room temperature, the compound 38B (300 mg, 0.78 mmol) was dissolved in Py/Ac$_2$O (2 ml, v/v=1:1) and DMAP (10 mg, 0.08 mmol) was added. After completion of the addition, the system was allowed to react at room temperature for 5 hrs. The starting material disappeared and the reaction was stopped. Ethyl acetate was added to dissolve the system. The resulting solution washed with 1 N HCl, saturated NaHCO$_3$ and NaCl solutions, dried and concentrated, resulting in 390 mg of the target compound 39B, with a yield of 97%.

$^1$H NMR (400 MHz, Chloroform-d) δ 7.43-7.22 (m, 5H), 6.14 (ddd, J=10.0, 5.7, 2.9 Hz, 1H), 5.53 (t, J=3.0 Hz, 1H), 5.19 (dd, J=6.3, 3.0 Hz, 1H), 4.91-4.80 (m, 1H), 4.62 (d, J=12.3 Hz, 1H), 4.51 (d, J=12.3 Hz, 1H), 4.14 (dd, J=10.1, 6.3 Hz, 1H), 3.85 (p, J=6.1 Hz, 1H), 3.66 (ddd, J=9.9, 5.7, 2.9 Hz, 2H), 3.58 (dd, J=11.1, 5.7 Hz, 1H), 3.49 (td, J=10.0, 4.4 Hz, 1H), 2.21 (s, 3H), 2.03 (s, 3H), 1.96 (s, 3H), 1.81-1.50 (m, 4H), 1.18 (d, J=6.2 Hz, 3H), 1.09 (d, J=6.1 Hz, 3H).

EXAMPLE 12. PREPARATION OF COMPOUND 40

39B

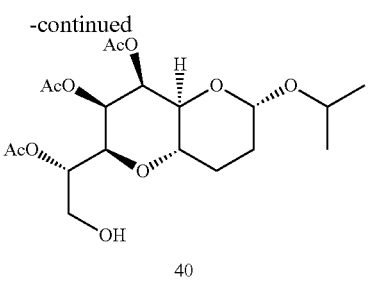

40

The Compound 39B (260 mg, 0.51 mmol) was dissolved in THF (5 ml) and Pd/C (13 mg) was added, followed by a catalytic hydrogenation at normal temperature and under atmospheric pressure. By being monitored by TLC, the reaction was completed after about 8 hrs, filtered, dried and concentrated, followed by column chromatography separation, resulting in 210 mg of the compound 40, with a yield of 98%.

$^1$H NMR (500 MHz, Chloroform-d) δ 6.13-5.89 (m, 1H), 5.56 (d, J=2.9 Hz, 1H), 5.22 (dd, J=6.5, 3.0 Hz, 1H), 4.89 (s, 1H), 4.19 (dd, J=9.9, 6.4 Hz, 1H), 3.86 (dd, J=13.1, 6.6 Hz, 3H), 3.70 (dd, J=9.9, 2.9 Hz, 1H), 3.66-3.55 (m, 1H), 2.21 (s, 3H), 2.07 (s, 3H), 1.98 (s, 3H), 1.88 (s, 1H), 1.79 (m, 3H), 1.20 (d, J=6.2 Hz, 3H), 1.12 (d, J=6.1 Hz, 3H).

EXAMPLE 13. PREPARATION OF COMPOUND 42

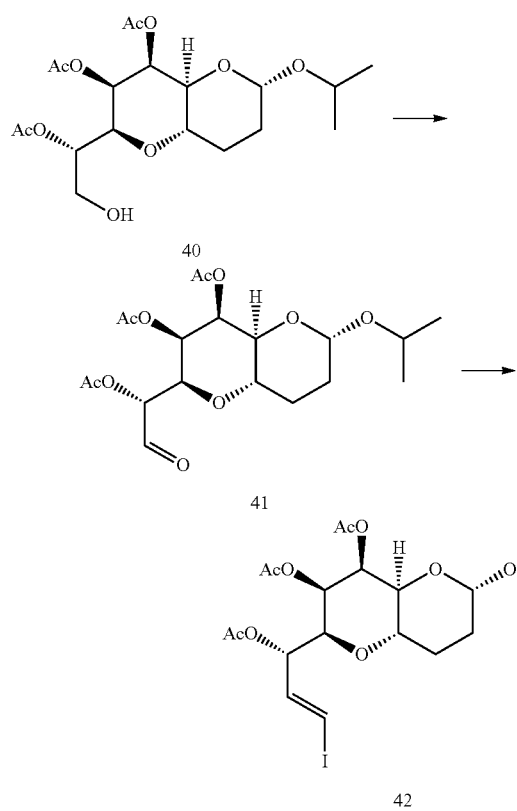

1) DMSO (1.26 mL, 19.8 mmol) was added into dry DCM (18 mL). The resulting mixture was placed in an acetone dry-ice bath and chilled down to −78° C. A solution of oxalyl chloride (1.13 mL, 13.4 mmol) in DCM (18 mL) was dropped. After end of the dropping, the reaction was kept at −78° C. to react for 30 min. A solution of the compound 40 (3.73 g, 8.9 mmol) as the starting material in DCM (18 mL) was dropped. After end of the dropping, the reaction was kept at −78° C. to react for 1 h. A solution of triethylamine (6.17 ml, 44.5 mmol) in DCM (18 mL) was dropped. After end of the dropping, the reaction was warmed up to room temperature to proceed for 30 min. Disappearance of the starting material speck was monitored by TLC. The reaction was quenched by adding the saturated NaHCO$_3$ solution and subjected to liquid separation. The aqueous phase was extracted with DCM two times. The resulting organic phases were pooled, dried, filtered, concentrated and used directly in the next reaction step.

2) CrCl$_2$ (5.47 g, 44.5 mmol) was placed into a round-bottomed flask under argon gas protection and suspended by adding a mixed solvent of THF and dioxane (54 mL, v/v=1/3). Then the reaction flask was placed in an ice-water bath and chilled down, followed by dropping a solution of the starting material 41 and CHIS (7.01 g, 19.8 mmol) in dioxane. The reaction solution was warmed slowly to room temperature to proceed over night (12-16 hrs). After completion of the reaction, the reaction was quenched by adding water, subjected to liquid separation, and extracted with ethyl acetate. The resulting organic phases were pooled, dried, filtered, and concentrated. 2.64 g of the compound 42 was obtained by column chromatography purification, with a yield of about 55% for the two-step reaction.

$^1$H NMR (500 MHz, Chloroform-d) δ 6.61 (d, J=3.8 Hz, 2H), 6.28 (d, J=8.5 Hz, 1H), 5.55 (d, J=3.7 Hz, 1H), 5.17 (dd. J=6.3, 3.1 Hz, 1H), 4.88 (s, 1H), 4.03 (dd, J=9.3, 6.2 Hz, 1H), 3.94-3.79 (m, 1H), 3.68 (dd, J=10.2, 2.7 Hz, 1H), 3.49 (s, 1H), 2.22 (s, 3H), 2.03 (s, 3H), 1.96 (s, 3H), 1.79-1.72 (m, 4H), 1.20 (d, J=6.2 Hz, 3H), 1.11 (d, J=6.0 Hz, 3H).

EXAMPLE 14. PREPARATION OF COMPOUNDS 43-45

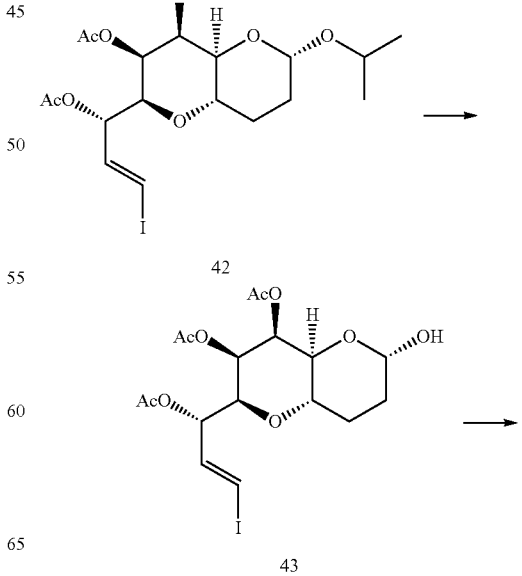

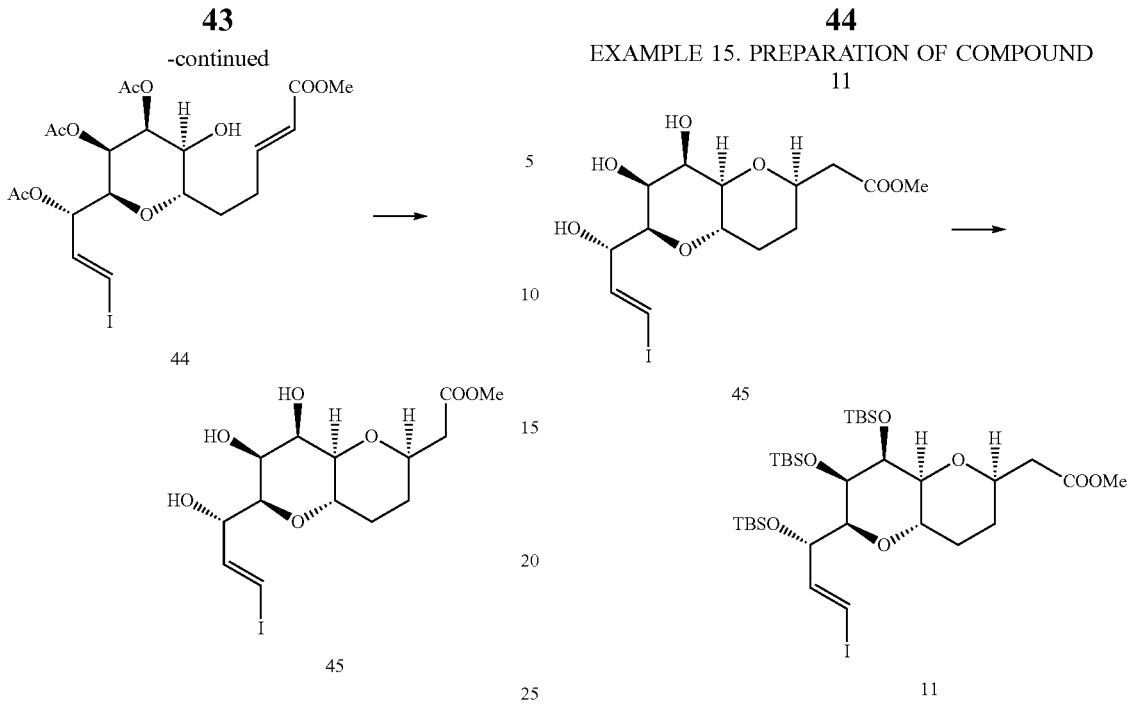

1) The starting material 42 (540 mg, 1 mmol) was added into a round-bottomed flask. 80% TFA aqueous solution (5 mL) was added at room temperature. The reaction system was kept at room temperature to proceed for 15 min before disappearance of the starting material speck demonstrated by TLC. The reaction flask was cooled in an ice water-bath. The reaction was quenched by adding the saturated sodium bicarbonate solution and extracted with ethyl acetate 2 times. The organic phases were pooled and washed again with the saturated sodium bicarbonate solution and the saturated sodium chloride solution, dried, filtered, and concentrate, obtaining the target Compound 43.

2) The Compound 43 was dissolved in toluene (10 mL). Methyl (triphenylphosphoranylidene) acetate (668 mg, 2 mmol) was added at room temperature with stirring and the resulting reaction was heated to reflux for 1 h. Disappearance of the starting material speck was demonstrated by TLC, obtaining the compound 44.

3) The reaction flask was cooled in an ice water-bath. A 40% solution of Triton B in methanol (1.36 g, 6 mmol) was added. After end of the dropping, the reaction was warmed up to room temperature to proceed. The reaction was kept at room temperature for 6 hrs before being stopped.

The reaction flask was cooled in an ice water-bath. The reaction was quenched by adding 0.5 M HCl and extracted with DCM 3-4 times. The organic phases were pooled and washed with the saturated sodium bicarbonate solution and the saturated sodium chloride solution, dried, filtered, and concentrated. With column chromatography separation, 205 mg of the white solid 45 was obtained, with a yield of about 48% for the three-step reaction.

$^1$H NMR (500 MHz, Chloroform-d) δ 6.70 (dd, J=14.5, 6.4 Hz, 1H), 6.48 (d, J=14.5 Hz, 1H), 5.23-4.98 (m, 1H), 4.28 (s, 1H), 4.03 (td, J=6.6, 3.3 Hz, 1H), 3.90 (t, J=8.7 Hz, 2H), 3.77 (dd, J=8.9, 6.2 Hz, 1H), 3.70 (s, 3H), 3.50 (m, 2H), 3.10 (dd, J=9.7, 2.8 Hz, 1H), 2.92 (s, 1H), 2.59 (dd, J=15.5, 7.6 Hz, 1H), 2.46 (dd, J=15.5, 5.1 Hz, 1H), 2.02 (p, J=4.1 Hz, 1H), 1.91-1.80 (m, 1H), 1.44 (t, J=9.6 Hz, 2H).

EXAMPLE 15. PREPARATION OF COMPOUND 11

The starting material 45 (923 mg, 2.2 mmol) was dissolved in anhydrous DCM (22 mL). Then the reaction flask was cooled in an ice water-bath. Firstly, 2, 6-dimethylpyridine (1.52 mL, 13.2 mmol) was added and then TBSOTf (1.74 mL, 9.9 mmol) was dropped. After end of the dropping, the reaction was warmed up to room temperature to proceed. Disappearance of the starting material speck was demonstrated by TLC after 1 h and the reaction was completed. The reaction was quenched by adding 2 N KHSO$_4$ solution, subjected to liquid separation, and extracted with DCM two times. The organic phases were pooled, dried, filtered, and concentrated. 1.52 g of the compound 11 was obtained by column chromatography purification, with a yield of about 90%.

$^1$H NMR (400 MHz, Acetone-d$_6$) δ 6.85 (ddd, J=14.6, 7.9, 1.3 Hz, 1H), 6.34 (dt, J=14.5, 1.2 Hz, 1H), 4.97 (dd, J=7.9, 3.8 Hz, 1H), 4.12 (q, J=2.0 Hz, 1H), 4.00 (ddd, J=7.0, 2.7, 1.4 Hz, 1H), 3.89-3.68 (m, 2H), 3.60 (d, J=1.3 Hz, 3H), 3.46 (d, J=4.6 Hz, 1H), 3.00 (dt, J=9.5, 1.7 Hz, 1H), 2.59-2.38 (m, 1H), 2.10-1.98 (m, 1H), 1.85 (dt, J=12.6, 4.0 Hz, 1H), 1.82-1.69 (m, 1H), 1.30 (dt, J=8.6, 1.5 Hz, 1H), 1.28-1.24 (m, 1H), 0.96 (d, J=1.4 Hz, 9H), 0.94 (d, J=1.3 Hz, 9H), 0.87 (d, J=1.3 Hz, 9H), 0.15 (d, J=1.5 Hz, 7H), 0.12 (d, J=1.4 Hz, 3H), 0.07 (d, J=1.3 Hz, 3H), 0.04 (d, J=1.3 Hz, 3H).

EXAMPLE 16. PREPARATION OF COMPOUND 46

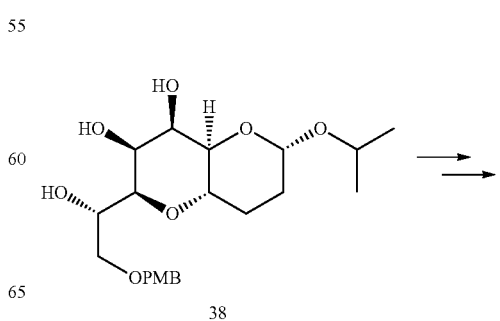

38

45

-continued

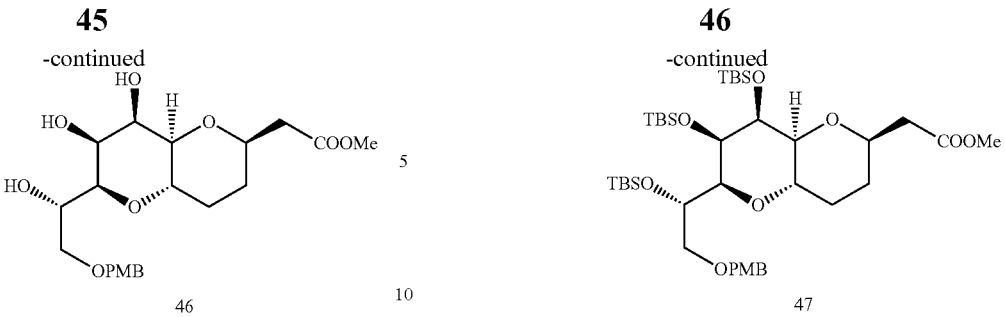

46

The Compound 38 (1 g, 2.4 mmol) was dissolved in THF (40 mL) at room temperature. 1 N HCl (12 mL) was added with stirring. The reaction system was heated to 55° C. to react. After 1 h the starting material disappeared. The reaction was stopped, cooled to room temperature, and subjected to liquid separation. The organic phase was dried over anhydrous sodium sulphate and the solvent was evaporated off under the reduced pressure, obtaining oily substance 38-1 for use in the next reaction step. 38-1 was dissolved in dry methanol (10 mL), methyl (triphenylphosphoranylidene) acetate (890 mg, 2.6 mmol) was added. The resulting reaction system was heated to reflux. After 6 h, the starting material disappeared and the reaction was stopped. The solvent was evaporated off under the reduced pressure, followed by adding 15 ml of toluene, and evaporated off again, resulting in 38-2 which can be used without purification in the next reaction step. 38-2 was dissolved in dry THF (50 mL). The resulting reaction system was cooled in an ice water-bath. A 40% solution of Triton B in methanol (3.29 g, 7.27 mmol) was added with stirring. The reaction proceeded at 0° C. for 20 min and then warmed up to room temperature to proceed for 3 h. The reaction was quenched by adding 2 N HCl in an ice water-bath (pH=5-6). Part of the solvent was evaporated off under the reduced pressure. The resulting residue was extracted with dichloromethane. The resulting extract was dried over anhydrous sodium sulphate, filtered and concentrated prior to separation on a silica gel column, resulting in 402 mg of the target product 46, with a yield of 38.8%.

$^1$H NMR (400 MHz, CDCl$_3$) δ 7.26 (d, J=8 Hz, 2H), 6.87 (d, J=8 Hz, 2H), 4.86-4.81 (m, 1H), 4.50 (s, 2H), 4.22 (s, 1H), 3.95-3.90 (m, 1H), 3.88-3.82 (m, 2H), 3.80 (s, 3H), 3.68 (s, 3H), 3.63 (dd, J=8 Hz, J=4 Hz, 1H), 3.53-3.47 (m, 3H), 3.05 (dd, J=8 Hz, J=4 Hz, 1H), 2.62 (dd, J=16 Hz, J=8 Hz, 1H), 2.44 (dd, J=16 Hz, J=8 Hz, 1H), 1.93-1.75 (m, 2H), 1.42-1.38 (m, 2H).

EXAMPLE 17. PREPARATION OF COMPOUND 47

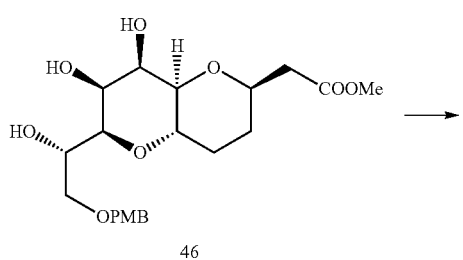

46

Under protection with argon gas, the Compound 46 (810 mg, 1.9 mmol) was dissolved in dry DCM (8 mL). 2,6-dimethylpyridine (1.22 g, 11.4 mmol) was added. Then TBSOTf (2.11 g, 9.5 mmol) was dropped slowly. After completion of the addition, the reaction was warmed up spontaneously to room temperature to proceed. After 1 h, the starting material disappeared and the reaction was stopped. The reaction was quenched by adding 0.5 M KHSO$_4$ and extracted with DCM, prior to separation with silica gel column chromatography, resulting in 1.3 g of the target Compound 47, with a yield of 92%.

$^1$H NMR (400 MHz, CDCl$_3$) δ7.27 (d, J=8 Hz, 2H), 6.86 (d, J=8 Hz, 2H), 4.56-4.54 (m, 1H), 4.43 (dd, J=32 Hz, J=8 Hz, 2H), 4.15-4.13 (m, 1H), 4.06 (s, 1H), 3.96-3.92 (m, 2H), 3.86-3.81 (m, 4H), 3.69 (s, 3H), 3.53-3.49 (m, 1H), 3.45-3.41 (m, 1H), 2.99-2.97 (m, 1H), 2.54 (dd, J=15 Hz, J=5 Hz, 1H), 2.38 (dd, J=15 Hz, J=5 Hz, 1H), 1.99-1.97 (m, 1H), 1.76-1.74 (m, 1H), 1.40-1.25 (m, 2H), 0.94-0.86 (m, 27H), 0.12-0.03 (m, 18H).

EXAMPLE 18. PREPARATION OF COMPOUND 48

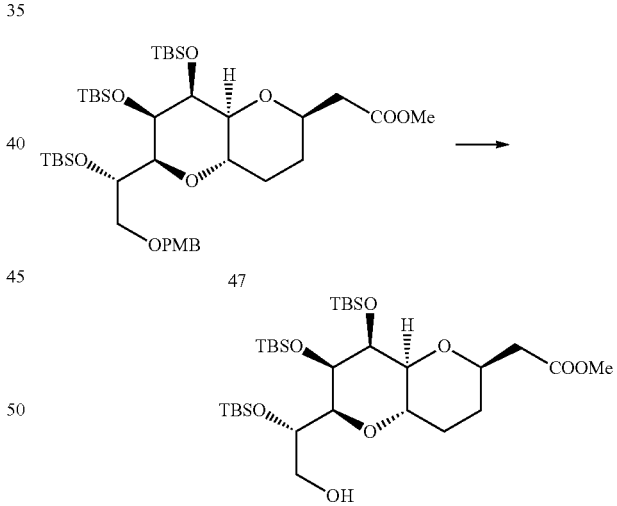

The Compound 47 (418 mg, 0.54 mmol) was dissolved in DCM/H$_2$O (6 ml, v/v=10/1) and cooled in an ice-water bath. DDQ (308 mg, 1.35 mmol) was added with stirring. After completion of the addition, the reaction was warmed up spontaneously to room temperature. The reaction was stopped after 1 h and the saturated sodium bicarbonate solution was added, while being cooled in the ice water-bath. The resulting mixture was extracted with DCM, dried, and concentrated prior to separation on a silica gel column, resulting in 255 mg of the target Compound 48, with a yield of 72%.

¹H NMR (400 MHz, CDCl₃) δ 4.43-4.40 (m, 1H), 4.07-4.02 (m, 2H), 3.98 (dd, J=8 Hz, J=4 Hz, 1H), 3.92 (dd, J=8 Hz, J=4 Hz, 1H), 3.86-3.81 (m, 2H), 3.67 (s, 3H), 3.64-3.58 (m, 1H), 2.97 (dd, J=8 Hz, J=4 Hz, 1H), 2.53 (dd, J=16 Hz, J=8 Hz, 1H), 2.40-2.34 (m, 2H), 2.05-2.02 (m, 1H), 1.78-1.72 (m, 1H), 1.41-1.36 (m, 2H), 0.93-0.90 (m, 27H), 0.12-0.08 (m, 18H).

EXAMPLE 19. PREPARATION OF COMPOUND 11

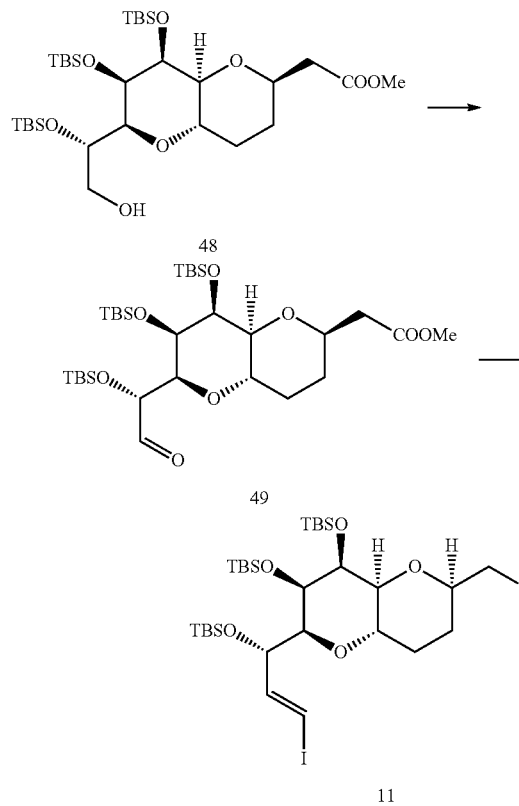

DMSO (0.14 mL, 2 mmol) was added into dry DCM (2 mL). The resulting mixture was placed in an acetone dry-ice bath and chilled down to −78° C. A solution of oxalyl chloride. (0.13 mL, 1.5 mmol) in DCM (2 mL) was dropped. After end of the dropping, the reaction was kept at −78° C. to react for 30 min. A solution of the starting material 48 (647 mg, 1 mmol) in DCM (2 mL) was dropped. After end of the dropping, the reaction was kept at −78° C. to react for 0.1 h. A solution of triethylamine (0.69 mL, 5 mmol) in DCM (2 mL) was dropped; After end of the dropping, the reaction was warmed up to room temperature to proceed for 30 min. The reaction was quenched by adding the saturated NaHCO₃ solution and subjected to liquid separation. The aqueous phases were extracted with DCM two times. The resulting organic phases were pooled, dried, filtered and concentrated, resulting the compound 49 for use directly in the next reaction step.

CrCl₂ (614 mg, 5 mmol) was placed into a round-bottomed flask under argon gas protection and added a mixed solvent of THF and dioxane (8 mL, v/v=1/3). Then the reaction flask was placed in an ice-water bath and chilled down, followed by dropping a solution of the starting material 49 and CHIS (787 mg, 2 mmol) in dioxane (6 mL). The reaction solution was warmed slowly to room temperature to react over night (12-16 hrs). The reaction still had the starting material remaining. The reaction was quenched by adding water, subjected to liquid separation, and extracted with ethyl acetate. The resulting organic phases were pooled, dried, filtered, and concentrated. 231 mg of the compound 11 was obtained by column chromatography purification with PE:EA=5:1, with a yield of about 30% for the two-step reaction.

¹H NMR (400 MHz, Acetone-d₆) δ 6.85 (ddd, J=14.6, 7.9, 1.3 Hz, 1H), 6.34 (dt, J=14.5, 1.2. Hz, 1H), 4.97 (dd, J=7.9, 3.8 Hz, 1H), 4.12 (q, J=2.0 Hz, 1H), 4.00 (ddd, J=7.0, 2.7, 1.4 Hz, 1H), 3.89-3.68 (m, 2H), 3.60 (d, J=1.3 Hz, 3H), 3.46 (d, J=4.6 Hz, 1H), 3.00 (dt, J=9.5, 1.7 Hz, 1H), 2.59-2.38 (m, 1H), 2.10-1.98 (m, 1H), 1.85 (dt, J=12.6, 4.0 Hz, 1H), 1.82-1.69 (m, 1H), 1.30 (dt, J=8.6, 1.5 Hz, 1H), 1.28-1.24 (m, 1H), 0.96 (d, J=1.4 Hz, 9H), 0.94 (d, J=1.3 Hz, 9H), 0.87 (d, J=1.3 Hz, 9H), 0.15 (d, J=1.5 Hz, 7H), 0.12 (d, J=1.4 Hz, 3H), 0.07 (d, J=1.3 Hz, 3H), 0.04 (d, J=1.3 Hz, 3H).

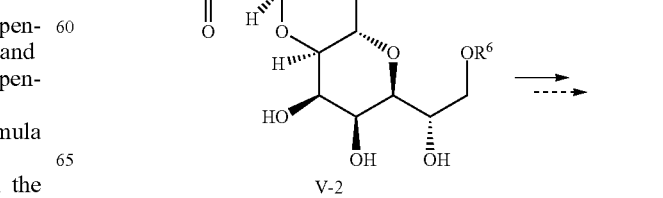

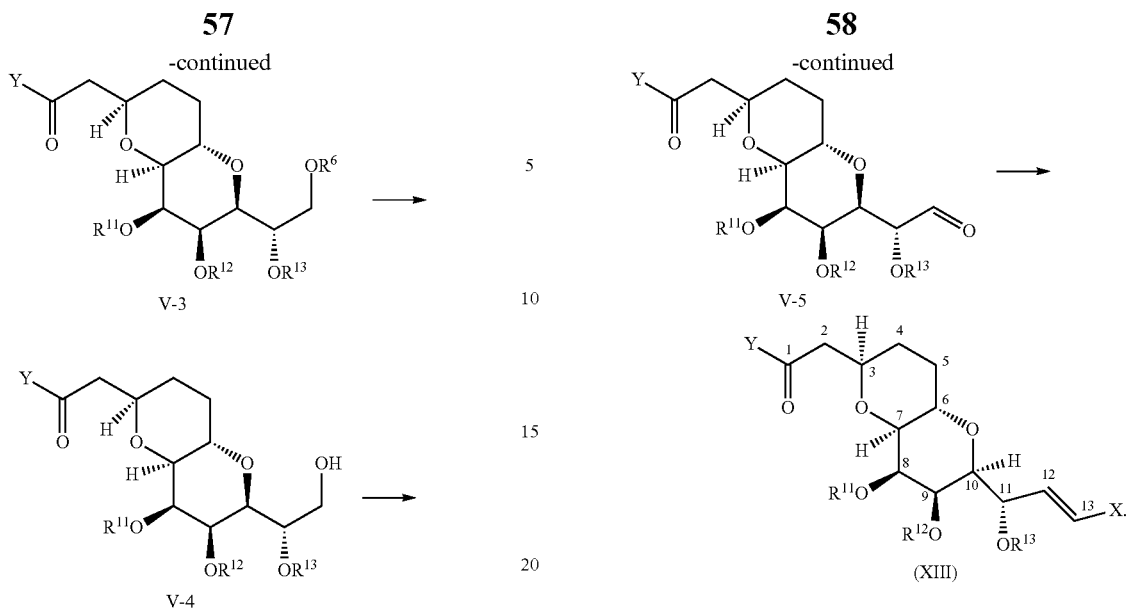

The invention claimed is:

1. A method for preparing a compound of formula (V), comprising:

reacting a compound of formula (IV) with $B_2(OR^7)_4$ to obtain a compound of formula (IV-1), and removing the group —$B(OR^7)_2$ from the compound of formula (IV-1) to obtain the compound of formula (V):

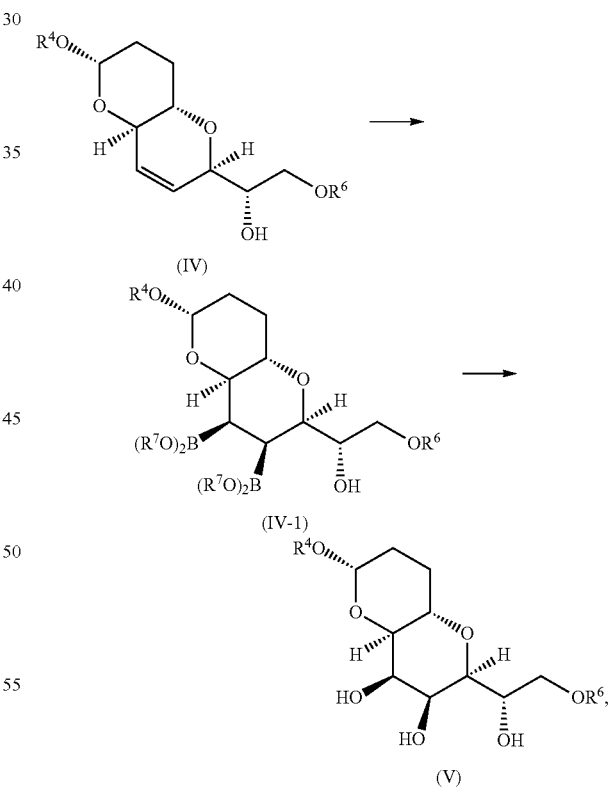

wherein $R^4$ and $R^6$ are the same or different and independently selected from hydroxyl protecting groups;
wherein the $R^7$ groups in the compound of formula (IV-1) are independently an alkyl unsubstituted or optionally substituted with one or more of $R^a$; or,
in each of two —$B(OR^7)_2$ groups, the two adjacent $R^7$ groups bind to each other to form an alkylidene unsubstituted or optionally substituted with one or more of R$^a$, two ends of said alkylidene each binding to the O atom via a chemical bond to form a ring with the B atom; and the R$^a$ groups are independently selected from —F, —Cl, —Br, —I, =O, alkyl, cycloalkyl, heterocycyl, aryl, heteroaryl, alkoxy, alkenyloxy, cycloalkoxy, heterocyclyloxy, aryloxy, heteroaryloxy, cycloalkylalkyl, heterocyclylalkyl, arylalkyl, and heteroarylalkyl.

2. A method for preparing a compound of formula (VI), comprising the step of:

preparing the compound of formula (V) according to the method of claim 1;

reacting the compound of formula (V) with a hydroxyl-protecting agent to obtain a compound of formula (VI)

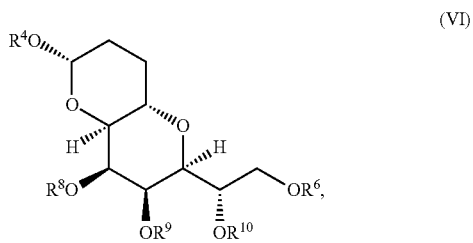

(VI)

wherein R$^8$, R$^9$, and R$^{10}$ are the same or different and independently selected from hydroxyl protecting groups.

3. A method for preparing a compound of formula (VIII), comprising the steps of:

preparing the compound of formula (VI) according to the method of claim 2;

reacting the compound of formula (VI) under a condition for removing the R$^6$ group to obtain a compound of formula (VII)

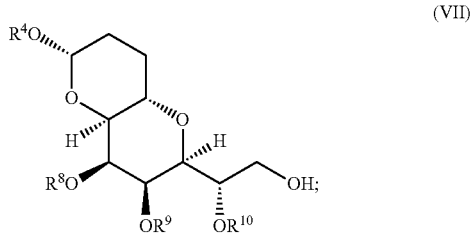

(VII)

and reacting the compound of formula (VII) in the presence of the oxidizing agent to obtain a compound of formula (VIII)

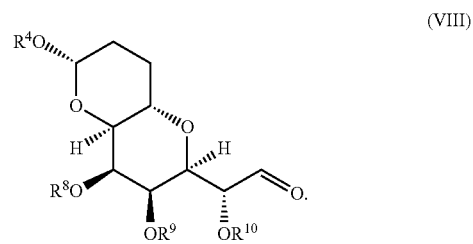

(VIII)

4. A method for preparing a compound of formula (IX), comprising the step of:

preparing the compound of formula (VIII) according to the method of claim 3;

reacting the compound of formula (VIII) to obtain a compound of formula (IX)

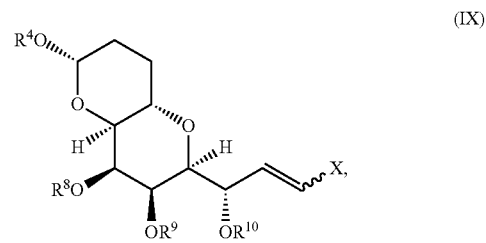

(IX)

X is selected from Cl, Br, I and R$^{14}$S(O)$_2$—, and

R$^{14}$ is selected from alkyl, cycloalkyl, heterocyclyl, aryl, heteroaryl unsubstituted, and heteroaryl substituted with one or more of R$^a$.

5. A method for preparing a compound of formula (XIII), comprising the steps of:

preparing the compound of formula (IX) according to the method of claim 4;

reacting the compound of formula (IX) to obtain a compound of formula (X)

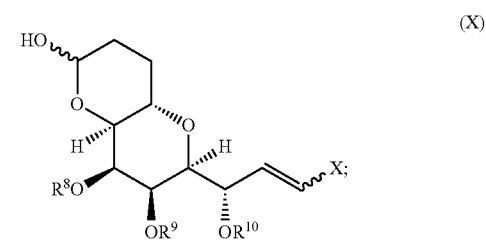

(X)

and reacting the compound of formula (X) to obtain a compound of formula (XI) and/or tautomeric isomers thereof

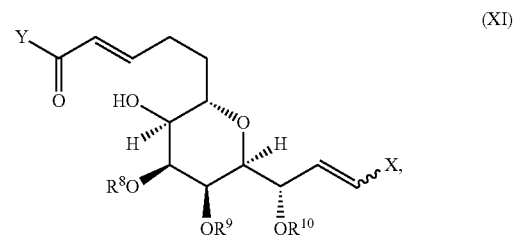

(XI)

wherein Y is an unsubstituted alkoxy or an alkoxy substituted with one or more of R$^a$; and reacting the compound of formula (XI) to obtain a compound of formula (XII)

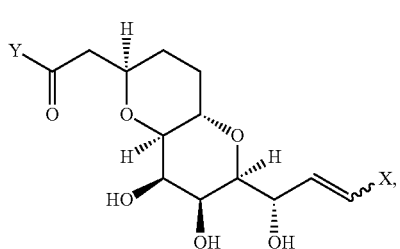
(XII)

wherein X, Y are defined in the same way as in the formula (XI); and reacting the compound of formula (XII) with the hydroxyl-protecting agent to obtain the compound of formula (XIII)

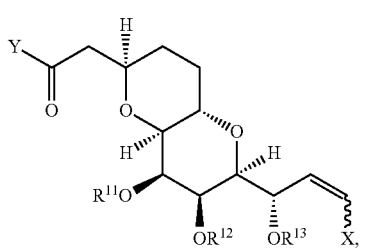
(XIII)

wherein X and Y are defined in the same way as in the formula (XI), and $R^{11}$, $R^{12}$, and $R^{13}$ are the same or different and independently selected from hydroxyl protecting groups.

6. A compound selected from

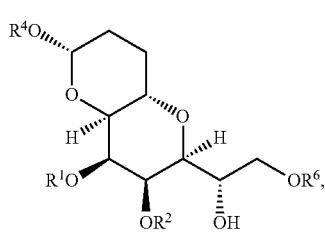
(V)

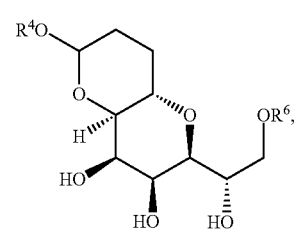
V-1

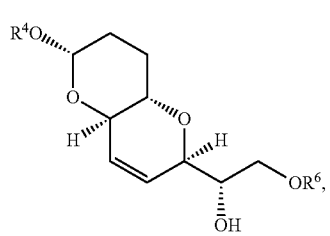
(IV)

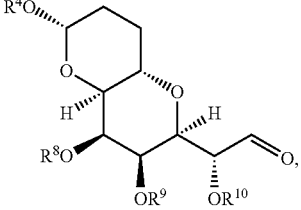
(VI)

(VII)

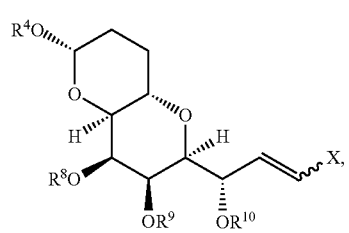
(VIII)

(IX)

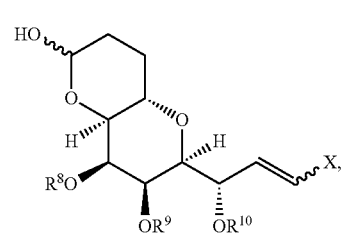
(X)

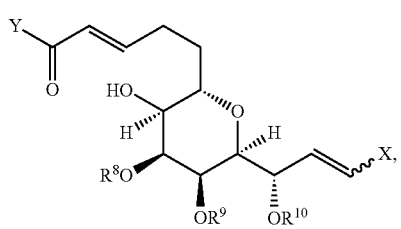
(XI)

and

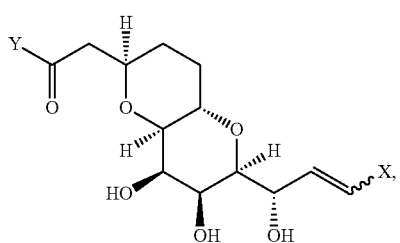
(XII)

wherein $R^1$ and $R^2$ are the same or different and independently selected from H and $—B(OR^7)_2$, $R^4$ and $R^6$ are the same or different and independently selected independently from hydroxyl protecting groups, wherein, in $—B(OR^7)_2$, $R^7$ is selected from an unsubstituted alkyl an alkyl optionally substituted with one or more of $R^a$; or two adjacent $R^7$ groups bind to each other to form an alkylidene unsubstituted or optionally substituted with one or more of $R^a$, two ends of said alkylidene each binding to the 0 atom via a chemical bond, thereby forming a ring with the B atom;

$R^8$, $R^9$, and $R^{10}$ are the same or different and independently selected from hydroxyl protecting groups, X is Cl, Br, I, or $R^{14}S(O)_2—$, $R^{14}$ is selected from alkyl, cycloalkyl, heterocyclyl, aryl, unsubstituted heteroaryl, and heteroaryl substituted with one or more of $R^a$ Y is an alkoxy unsubstituted or optionally substituted with one or more of $R^a$, and each of the $R^a$ is the same or different and independently selected independently of one another from —F, —Cl, —Br, —I, $=$O, alkyl, cycloalkyl, heterocycyl, aryl, heteroaryl, alkoxy, alkenyloxy, cycloalkoxy, heterocyclyloxy, aryloxy, heteroaryloxy, cycloalkylalkyl, heterocyclylalkyl, arylalkyl, and heteroarylalkyl.

7. The method of preparing the compound of formula (IV),

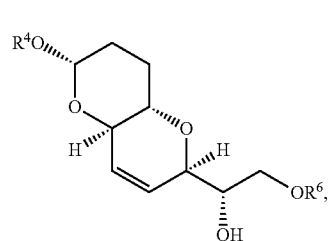
(IV)

wherein $R^4$ and $R^6$ are the same or different and independently selected from hydroxyl protecting groups, comprising the steps of:

1) selectively epoxidized a diene compound (III) or compound (III-4) at the positions $C_8$, $C_9$:

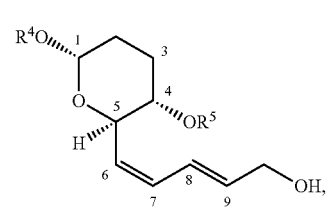
(III)

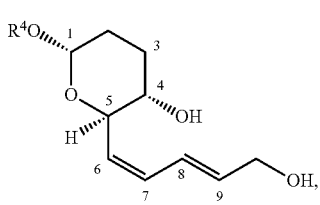
(III-4)

wherein $R^5$ is selected from hydroxyl protecting groups; or 2) causing a compound (III-3) or compound (III-5) to undergo an intra-molecular $S_N2$ reaction

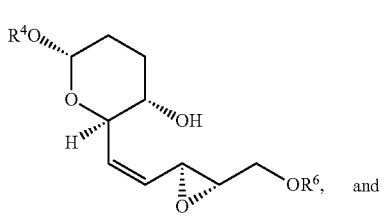
(III-3)

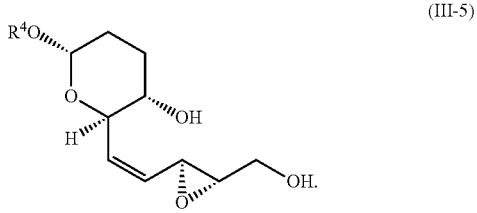
(III-5)

8. The method of preparing the compound of formula (IX), comprising the steps of:

reacting the compound of formula (VIII) to obtain the compound of formula (IX)

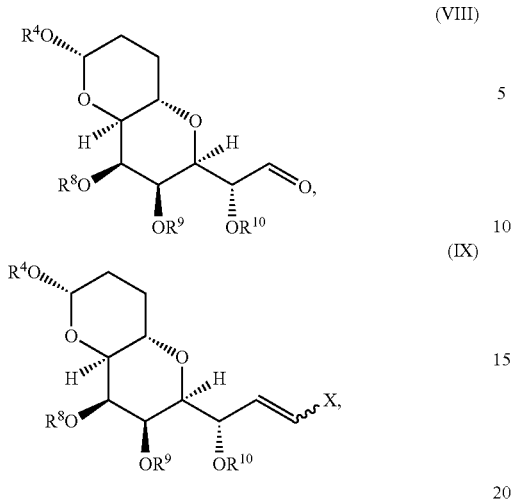

(VIII)

(IX)

wherein R⁴ is a hydroxyl protecting group,
R⁸, R⁹, and R¹⁰ are the same or different and independently selected from hydroxyl protecting groups,
X is Cl, Br, I or R¹⁴S(O)₂—,
R¹⁴ is selected from alkyl, cycloalkyl, heterocyclyl, aryl, unsubstituted heteroaryl, and heteroaryl substituted with one or more Rᵃ, and
each of the Rᵃ is the same or different and independently selected from —F, —Cl, —Br, —I, =O, alkyl, cycloalkyl, heterocycyl, aryl, heteroaryl, alkoxy, alkenyloxy, cycloalkoxy, heterocyclyloxy, aryloxy, heteroaryloxy, cycloalkylalkyl, heterocyclylalkyl, arylalkyl, and heteroarylalkyl.

9. The method of preparing the compound of formula (VII), comprising the steps of:
reacting the compound of formula (VI) to obtain the compound of formula (VII),

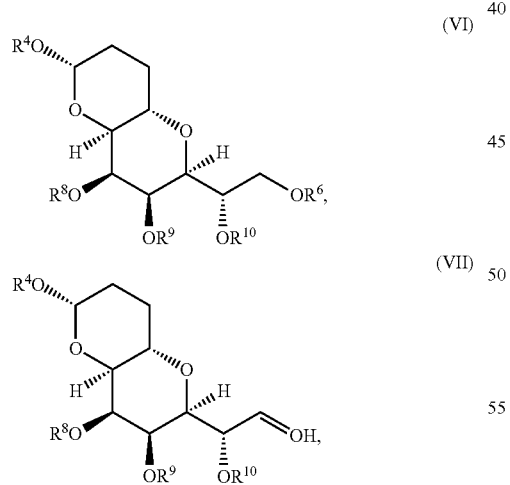

(VI)

(VII)

wherein R⁴ and R⁶ are the same or different and independently selected from hydroxyl protecting groups, and
R⁸, R⁹, and R¹⁰ are the same or different and independently selected from hydroxyl protecting groups.

10. The method of preparing the compound of formula (VIII), comprising the steps of:
reacting the compound of formula (VII) to obtain the compound of formula (VIII)

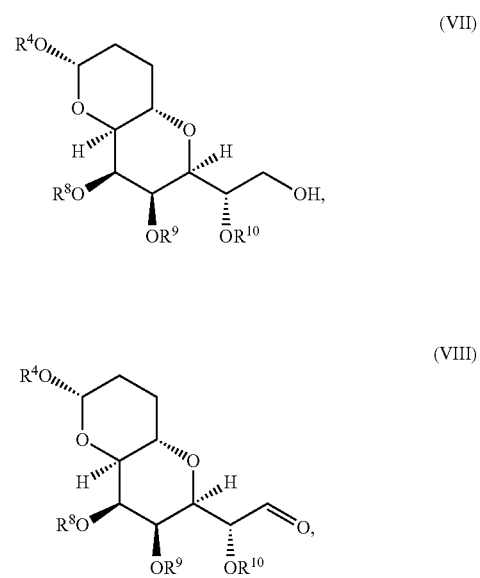

(VII)

(VIII)

R⁴ is a hydroxyl protecting group, and
R⁸, R⁹, and R¹⁰ are the same or different and independently selected from hydroxyl protecting groups.

11. A method for preparing a compound of formula (XIII), comprising:
preparing the compound of formula (V) according the method of claim 1;
removing the hydroxyl protecting group R⁴ from the compound of formula (V) to synthesize a compound (V-2);
subjecting the compound (V-2) to a stepwise or concurrent hydroxyl-protection to obtain a compound (V-3);
removing the protecting group R⁶ from the compound (V-3) to generate a compound (V-4);
oxidizing the compound (V-4) to form an aldehyde (V-5); and
reacting the aldehyde (V-5) to form the compound of formula (XIII):